US012672759B2

(12) United States Patent
Cummings et al.

(10) Patent No.: US 12,672,759 B2
(45) Date of Patent: Jul. 7, 2026

(54) SUCTION VALVE FOR MEDICAL DEVICES

(71) Applicant: Boston Scientific Scimed, Inc., Maple Grove, MN (US)

(72) Inventors: Nathan Thomas Cummings, Worcester, MA (US); Carolina Villarreal, Hopedale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/604,776

(22) Filed: Mar. 14, 2024

(65) Prior Publication Data

US 2024/0306888 A1     Sep. 19, 2024

Related U.S. Application Data

(60) Provisional application No. 63/490,700, filed on Mar. 16, 2023.

(51) Int. Cl.
*A61B 1/00* (2006.01)

(52) U.S. Cl.
CPC ................................. *A61B 1/00068* (2013.01)

(58) Field of Classification Search
CPC ......................... A61B 1/00068; A61B 1/00064
USPC .......................................................... 600/159
See application file for complete search history.

(56) References Cited

U.S. PATENT DOCUMENTS

| | | | |
|---|---|---|---|
| 11,300,216 B2 | 4/2022 | Harris et al. | |
| 11,576,566 B2 | 2/2023 | Pollock et al. | |
| 2020/0352415 A1 | 11/2020 | Harris et al. | |
| 2020/0355281 A1 | 11/2020 | Harris et al. | |
| 2022/0186846 A1 | 6/2022 | Harris et al. | |
| 2022/0192479 A1 | 6/2022 | Harris et al. | |
| 2022/0211256 A1 | 7/2022 | Wolfe | |
| 2022/0221069 A1 | 7/2022 | Ng | |
| 2022/0361734 A1 | 11/2022 | Ko | |

FOREIGN PATENT DOCUMENTS

WO        2021016385 A1      1/2021

OTHER PUBLICATIONS

International Search Report and Written Opinion for International Application No. PCT/US2024/019854, dated Jun. 13, 2024.

*Primary Examiner* — Paul J Gray
(74) *Attorney, Agent, or Firm* — Seager, Tufte & Wickhem, LLP

(57)        ABSTRACT

Suction valves for selectively fluidly coupling a suction pump with a working channel. An illustrative suction valve may comprise an elongate shaft having a longitudinal axis and extending from a first end to a second end, at least one aperture extending through a sidewall of the elongate shaft, a rigid base extending radially outward from an outer surface of the elongate shaft, and a compliant member extending between a first surface of the rigid base and the first end of the elongate shaft. In response to an applied force, the compliant member may be configured to compress to move the elongate shaft in a direction parallel to the longitudinal axis of the elongate shaft to a use configuration and in the absence of the applied force the compliant member may be configured to bias the elongate shaft to a rest configuration.

20 Claims, 17 Drawing Sheets

SUCTION VALVE FOR MEDICAL DEVICES

CROSS-REFERENCE TO RELATED APPLICATIONS

This application claims the benefit of U.S. Provisional patent application Ser. No. 63/490,700 filed on Mar. 16, 2023, the disclosure of which is incorporated herein by reference.

FIELD

This disclosure relates generally to medical devices, and particularly to a suction valve for use with an endoscope.

BACKGROUND

Conventionally, endoscope devices have been widely used for performing diagnostic and/or therapeutic treatments. During endoscopic procedures, physicians may use a combination of air, irrigation, and lens wash as a means of flushing debris, cleaning optics, and insufflating the working lumen. Suction valves may be used for operating a suction operation. Suction valves for typical endoscopes may have a rest state and an active state. In the rest state, the suction valve may seal off a working channel so that insufflation cannot easily leak out of the patient's lumen. In the active state, the suction valve may fluidly couple an endoscope working channel and a suction pump so that fluids and tissue samples may be removed from the patient's lumen. User input may be required to move the suction valve from the rest state to the active state. The suction valve may return to the rest state when the user input is released. During endoscopic procedures, the user may need to seal off the suction valve from the atmosphere of the room to produce therapeutic suction.

It may be desirable to provide a suction valve which provides a sealing surface to seal off the suction valve from the atmosphere of the room in the presence of user input and which returns to a rest state in the absence of a user input. It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first embodiment, a suction valve for a medical device may comprise an elongate shaft having a longitudinal axis and extending from a first end to a second end, the elongate shaft defining a lumen extending from the second end towards the first end thereof, at least one aperture extending through a sidewall of the elongate shaft, a rigid base extending radially outward from an outer surface of the elongate shaft, and a compliant member extending between a first surface of the rigid base and the first end of the elongate shaft. In response to an applied force, the compliant member may be configured to compress to move the elongate shaft in a direction parallel to the longitudinal axis of the elongate shaft to a use configuration and in the absence of the applied force the compliant member may be configured to bias the elongate shaft to a rest configuration.

Alternatively or additionally to any of the examples above, in another example, the at least one aperture may be positioned between a second surface of the rigid base and the second end of the elongate shaft.

Alternatively or additionally to any of the examples above, in another example, the rigid base may be positioned between the first end and the second of the elongate shaft.

Alternatively or additionally to any of the examples above, in another example, the suction valve may further comprise one or more orientation features extending from a second surface of the rigid base.

Alternatively or additionally to any of the examples above, in another example, the one or more orientation features comprise one or more protrusions extending generally parallel to the longitudinal axis to the elongate shaft.

Alternatively or additionally to any of the examples above, in another example, the suction valve may further comprise at least one fastening member extending from the rigid base, the at least one fastening member configured to engage a mating feature on a medical device.

Alternatively or additionally to any of the examples above, in another example, the at least one fastening member may comprise a clip.

Alternatively or additionally to any of the examples above, in another example, the at least one fastening member may be configured to form a snap fit with the mating feature on the medical device.

Alternatively or additionally to any of the examples above, in another example, the at least one fastening member may be formed as a single monolithic structure with the rigid base.

Alternatively or additionally to any of the examples above, in another example, the suction valve may further comprise at least one fastening member formed in the compliant member, the at least one fastening member configured to engage a mating feature on a medical device.

Alternatively or additionally to any of the examples above, in another example, the at least one fastening member may be formed as a single monolithic structure with the compliant member.

Alternatively or additionally to any of the examples above, in another example, the at least one aperture extending through a sidewall of the elongate shaft may comprise a first aperture and a second aperture, the first and second apertures may be circumferentially spaced about 180° from one another about the longitudinal axis of the elongate shaft.

Alternatively or additionally to any of the examples above, in another example, when the elongate shaft is in the use configuration, the at least one aperture may be aligned with an opening of a medical device.

Alternatively or additionally to any of the examples above, in another example, the rigid base may include one or more openings extending through a thickness thereof.

Alternatively or additionally to any of the examples above, in another example, when in the use configuration, the compliant member may compress to block the one or more openings in the rigid base.

Alternatively or additionally to any of the examples above, in another example, when in the rest configuration the compliant member may have an outer surface having a generally ovoid shape.

Alternatively or additionally to any of the examples above, in another example, when in the rest configuration the compliant member may have an outer surface having a generally cylindrical shape.

Alternatively or additionally to any of the examples above, in another example, when in the rest configuration the compliant member may have an outer surface having a generally hemispherical shape.

In another example, a suction valve for a medical device may comprise an elongate shaft having a longitudinal axis and extending from a first end to a second end, the elongate shaft defining a lumen extending from the first end to the second end thereof, at least one aperture extending through a sidewall of the elongate shaft, a rigid base extending radially outward from an outer surface of the elongate shaft, the rigid base positioned between the first end and the second end of the elongate shaft, at least one fastening member extending from the rigid base, the at least one fastening member configured to engage a mating feature on a medical device, and a compliant member extending between a first surface of the rigid base and the first end of the elongate shaft. In response to an applied force, the compliant member may be configured to compress to move the elongate shaft in a direction parallel to the longitudinal axis of the elongate shaft to a use configuration and in the absence of the applied force the compliant member may be configured to bias the elongate shaft to a rest configuration.

Alternatively or additionally to any of the examples above, in another example, the at least one aperture may be positioned between a second surface of the rigid base and the second end of the elongate shaft.

Alternatively or additionally to any of the examples above, in another example, the suction valve may further comprise one or more orientation features extending from a second surface of the rigid base.

Alternatively or additionally to any of the examples above, in another example, the one or more orientation features may comprise one or more protrusions extending generally parallel to the longitudinal axis to the elongate shaft.

Alternatively or additionally to any of the examples above, in another example, the at least one fastening member may be configured to form a snap fit with the mating feature on the medical device.

Alternatively or additionally to any of the examples above, in another example, the at least one fastening member may be formed as a single monolithic structure with the rigid base.

Alternatively or additionally to any of the examples above, in another example, when the elongate shaft is in the use configuration, the at least one aperture may be aligned with an opening of a medical device.

In another example, a suction valve for a medical device may comprise an elongate shaft having a longitudinal axis and extending from a first end to a second end, the elongate shaft defining a lumen extending from the first end to the second end thereof, at least one aperture extending through a sidewall of the elongate shaft, a rigid base extending radially outward from an outer surface of the elongate shaft, the rigid base positioned between the first end and the second end of the elongate shaft, a compliant member extending between a first surface of the rigid base and the first end of the elongate shaft, and at least one fastening member formed in the compliant member, the at least one fastening member configured to engage a mating feature on a medical device. In response to an applied force, the compliant member may be configured to compress to move the elongate shaft in a direction parallel to the longitudinal axis of the elongate shaft to a use configuration and in the absence of the applied force the compliant member may be configured to bias the elongate shaft to a rest configuration.

Alternatively or additionally to any of the examples above, in another example, the compliant member may have a generally cylindrical shape.

Alternatively or additionally to any of the examples above, in another example, the at least one fastening member may be formed as a single monolithic structure with the compliant member.

Alternatively or additionally to any of the examples above, in another example, when the elongate shaft is in the use configuration, the at least one aperture may be aligned with an opening of a medical device.

Alternatively or additionally to any of the examples above, in another example, the suction valve may further comprise one or more orientation features extending from a second surface of the rigid base.

In another example, a suction valve for a medical device may comprise an elongate shaft having a longitudinal axis and extending from a first end to a second end, the elongate shaft defining a lumen extending second end towards the first end thereof, at least one aperture extending through a sidewall of the elongate shaft, a rigid base including a platform region extending radially outward from an outer surface of the elongate shaft and an annular wall extending from an outer edge of the platform region and towards the first end of the elongate shaft, the platform region including one or more openings extending through a thickness thereof, and a compliant member extending between a first surface of the platform region and one or more ledges adjacent the first end of the elongate tubular shaft. In in response to an applied force, the compliant member may be configured to compress to move the elongate shaft in a direction parallel to the longitudinal axis of the elongate shaft to a use configuration and in the absence of the applied force the compliant member may be configured to bias the elongate shaft to a rest configuration.

Alternatively or additionally to any of the examples above, in another example, when in the use configuration, the compliant member may compress to block the one or more openings in the platform region.

Alternatively or additionally to any of the examples above, in another example, when in the use configuration, the complaint member may deform radially outward to contact an inner surface of the annular wall.

Alternatively or additionally to any of the examples above, in another example, when in the rest configuration, the compliant member may have a first cross-sectional dimension and when in the use configuration, the compliant member may have a second cross-sectional dimension, the second cross-sectional dimension may be greater than the first cross-sectional dimension.

Alternatively or additionally to any of the examples above, in another example, the suction valve may further comprise one or more orientation features extending from a second surface of the rigid base.

Alternatively or additionally to any of the examples above, in another example, the one or more orientation features may comprise one or more protrusions extending generally parallel to the longitudinal axis to the elongate shaft.

Alternatively or additionally to any of the examples above, in another example, the suction valve may further comprise at least one fastening member extending from the rigid base, the at least one fastening member configured to engage a mating feature on a medical device.

Alternatively or additionally to any of the examples above, in another example, the at least one fastening member may be configured to form a snap fit with the mating feature on the medical device.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
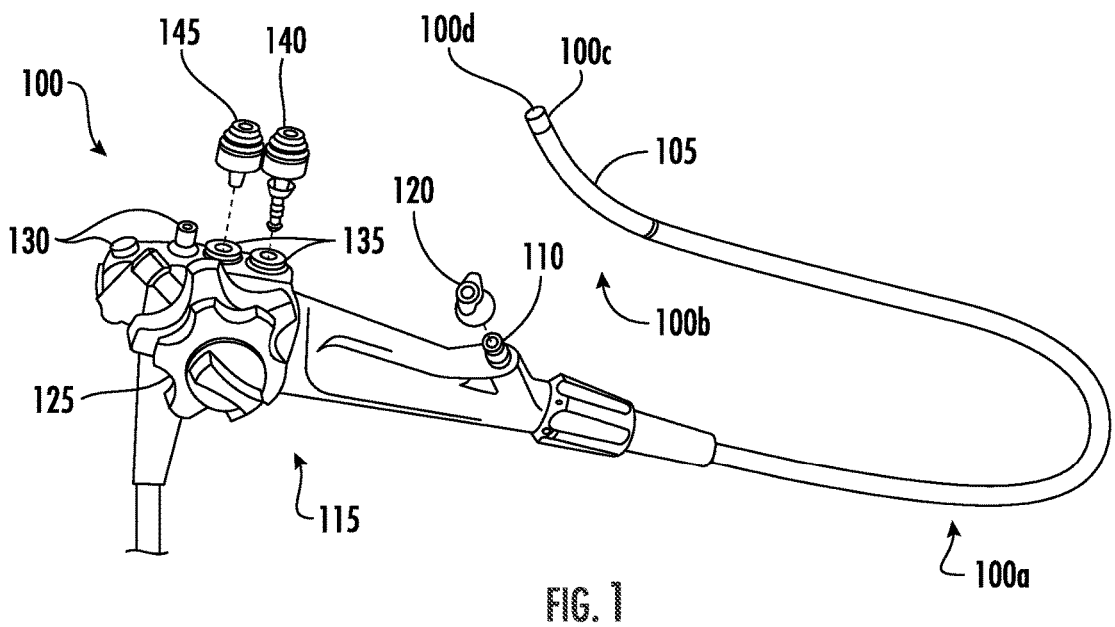
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a suction valve of an endoscope. It should be appreciated that such embodiments may be used to control the flow of fluid, for a variety of different purposes where it is desired to selectively fluidly couple one or more channels of a device.

Although the present disclosure includes descriptions of a suction valve suitable for use with an endoscope system to control suction to an endoscope, the devices, systems, and methods herein could be implemented in other medical systems requiring the selective fluid and/or gas coupling of various channels, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. Suction valves may be used for operating a suction operation. Suction valves for typical endoscopes may have a rest state and an active state. In the rest state, the suction valve may seal off a working channel so that insufflation cannot easily leak out of the patient's lumen. In the active state, the suction valve may fluidly couple an endoscope working channel and a suction pump so that fluids and tissue samples may be removed from the patient's lumen. User input may be required to move the suction valve from the rest state to the active state. The suction valve may return to the rest state when the user input is released. During endoscopic procedures, the user may need to seal off the suction valve from the atmosphere of the room to produce therapeutic suction.

Figure 2:
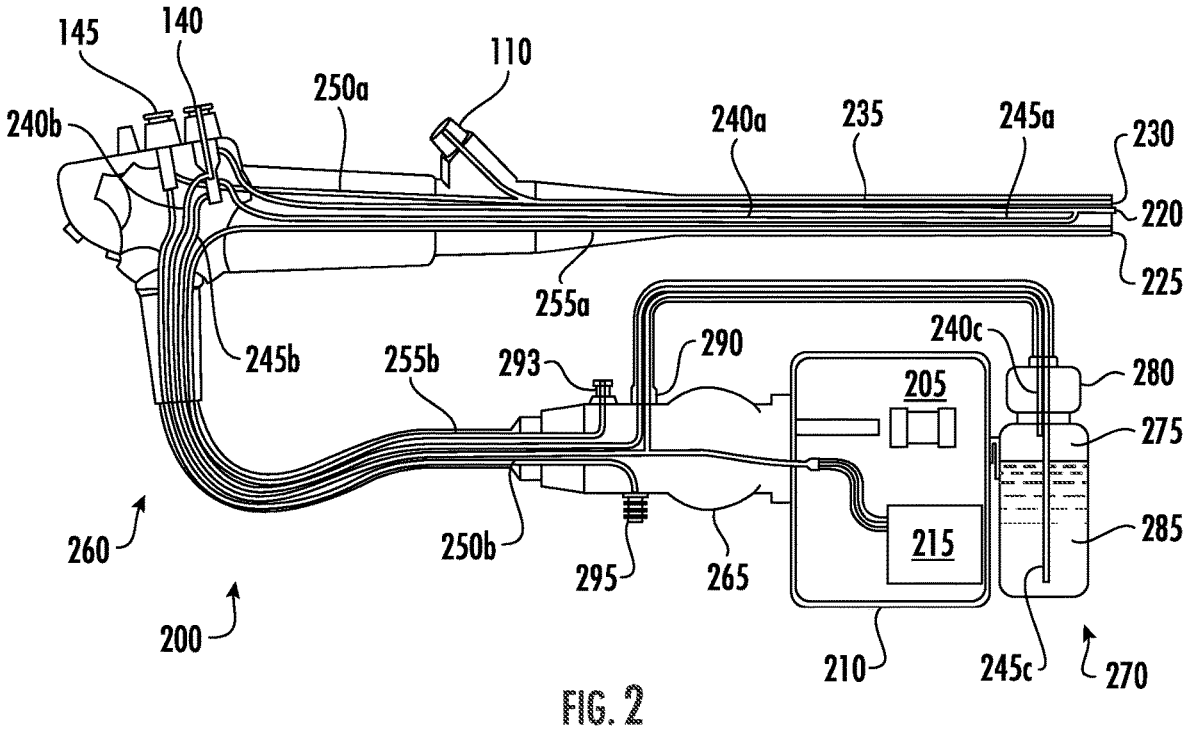
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100a that is inserted into a patient. A light source 205 feeds illumination light to a distal portion 100b of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip 100c of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, may also be included on the face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240a and a lens wash supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240b, a lens wash feed line 245b, a suction feed line 250b, an irrigation feed line 255b, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100a to transmit light to the distal tip 100c of the endoscope 100. The connector portion 265 when plugged into the video processing unit 210 also connects the air pump 215 to the gas feed line 240b in the umbilical 260.

A water reservoir or container 270 (e.g., water bottle) is fluidly connected to the endoscope 100 through the connector portion 265 and the umbilical 260. A length of gas supply tubing 240c passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240c. The gas feed line 240b from the umbilical 260 branches in the connector portion 265 to fluidly communicate with the gas supply tubing 240c at the detachable gas/lens wash connection 290, as well as the air pump 215. A length of lens wash supply tubing 245c, with one end positioned at the bottom of the reservoir 270, passes through the top 280 of the reservoir 270 to the same detachable connection 290 as the gas supply tubing 240c on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255b in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash supply tubing 245c may source water from the same reservoir. The connector portion 265 may also include a detachable suction connection 295 for suction feed line 250b and suction supply line 250a fluidly connecting a vacuum source (e.g., hospital house suction) (not shown) to the umbilical 260 and endoscope 100. The detachable suction connection 295 may be detachable from the connector portion 265 and/or the suction feed line 250b and/or the vacuum source.

The gas feed line 240b and lens wash feed line 245b are fluidly connected to the valve well 135 for the gas/water valve 140 and configured such that operation of the gas/water valve 140 in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240b in the umbilical 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash supply tubing 245c, through the connector portion 265, umbilical 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash supply tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255b in the umbilical 260 and the irrigation supply line 255a endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilical, and down the irrigation supply line in the shaft 100a of the endoscope to the distal tip 100c. In order to equalize the pressure in the water source as water is pumped out of the irrigation supply tubing, an air vent (not shown) may be included in the top 280 of the water reservoir 270.

The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash supply tubing 245c, may be placed in the path of the irrigation supply tubing to help prevent backflow into the reservoir after water has passed the valve. In some cases, irrigation water may be supplied from the water reservoir 270. Some illustrative systems where the supply tubing for irrigation and lens wash are connected to and drawn from a single water reservoir are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference.

When the suction valve 145 is in a neutral position or rest state, without the user's finger on and/or depressing the valve, air is allowed to flow into and/or out of the valve 145 to atmosphere. When suction is desired, the user's finger is used to block a vent to atmosphere as well as to depress the suction valve. Depressing the suction valve 145 may move the suction valve 145 within the valve well 135 to fluidly couple the working channel 235 with the suction pump (not explicitly shown) via the suction supply line 250a.

Figure 3:
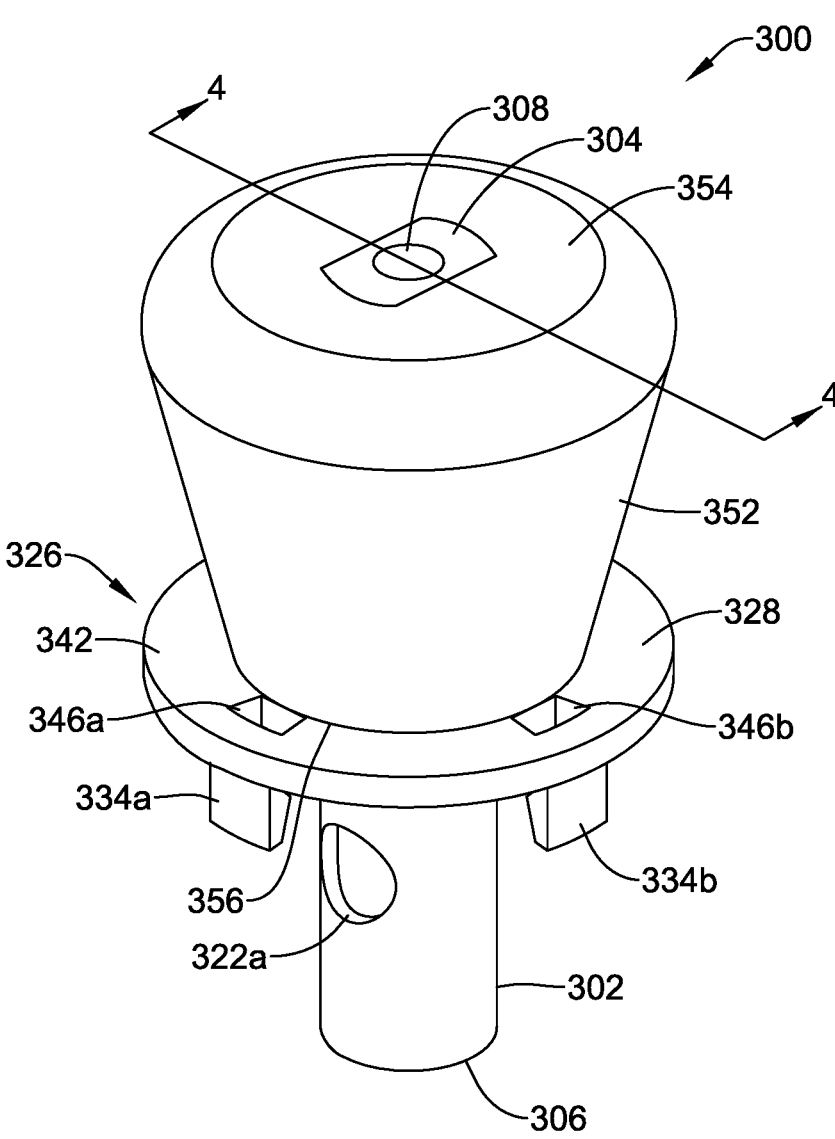
FIG. 3 depicts a top perspective view of an illustrative suction valve.
Figure 4:
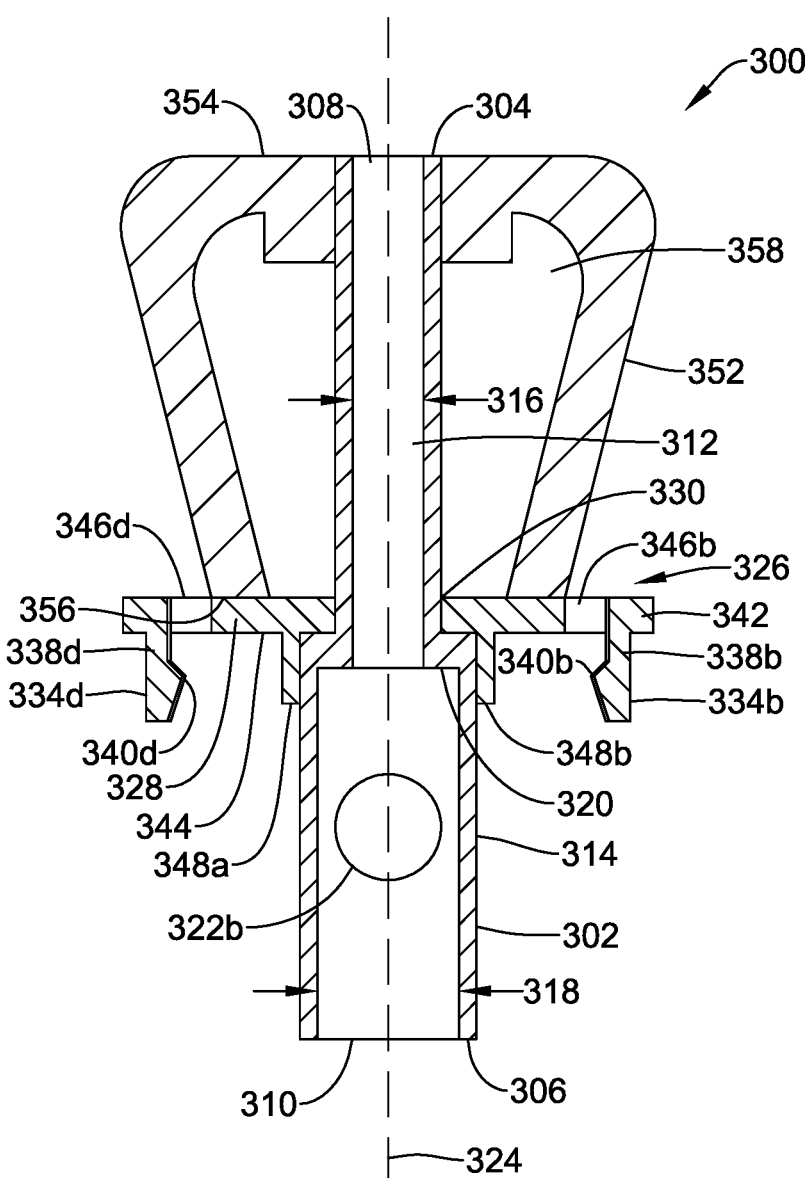
FIG. 4 depicts a cross-sectional view of the illustrative suction valve, taken at line 4-4 of FIG. 3.
Figure 5:
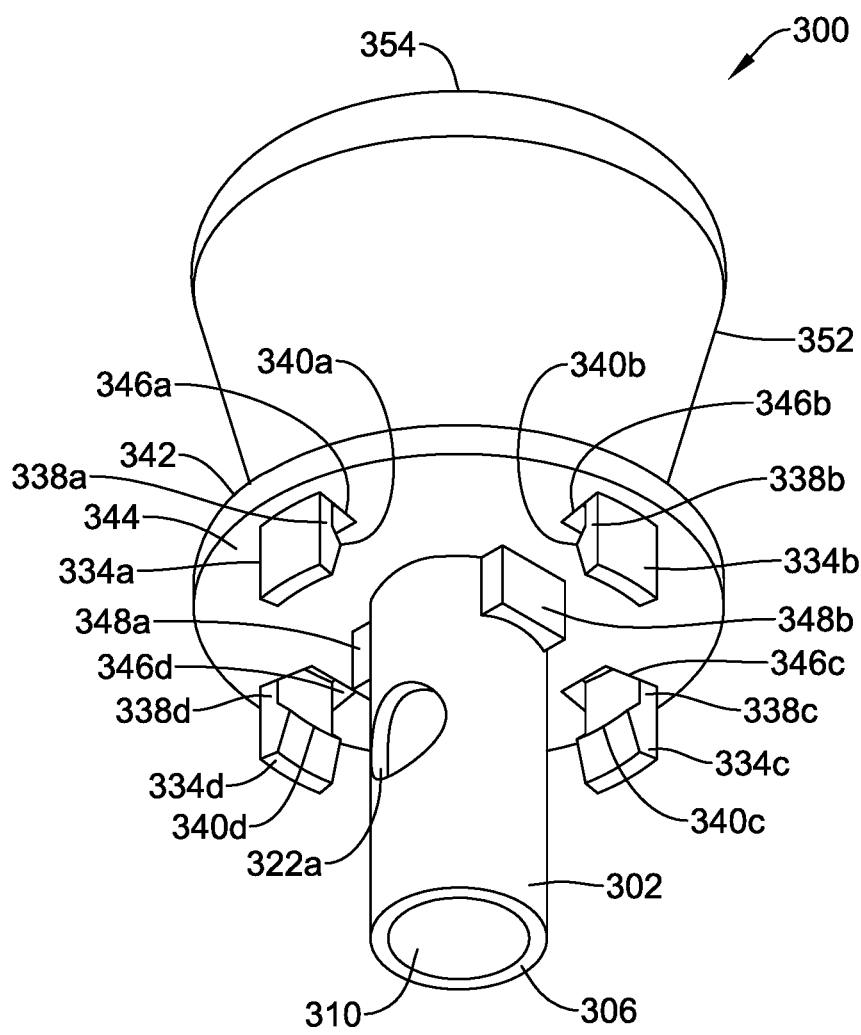
FIG. 5 depicts a bottom perspective view of the illustrative suction valve.
Figure 6:
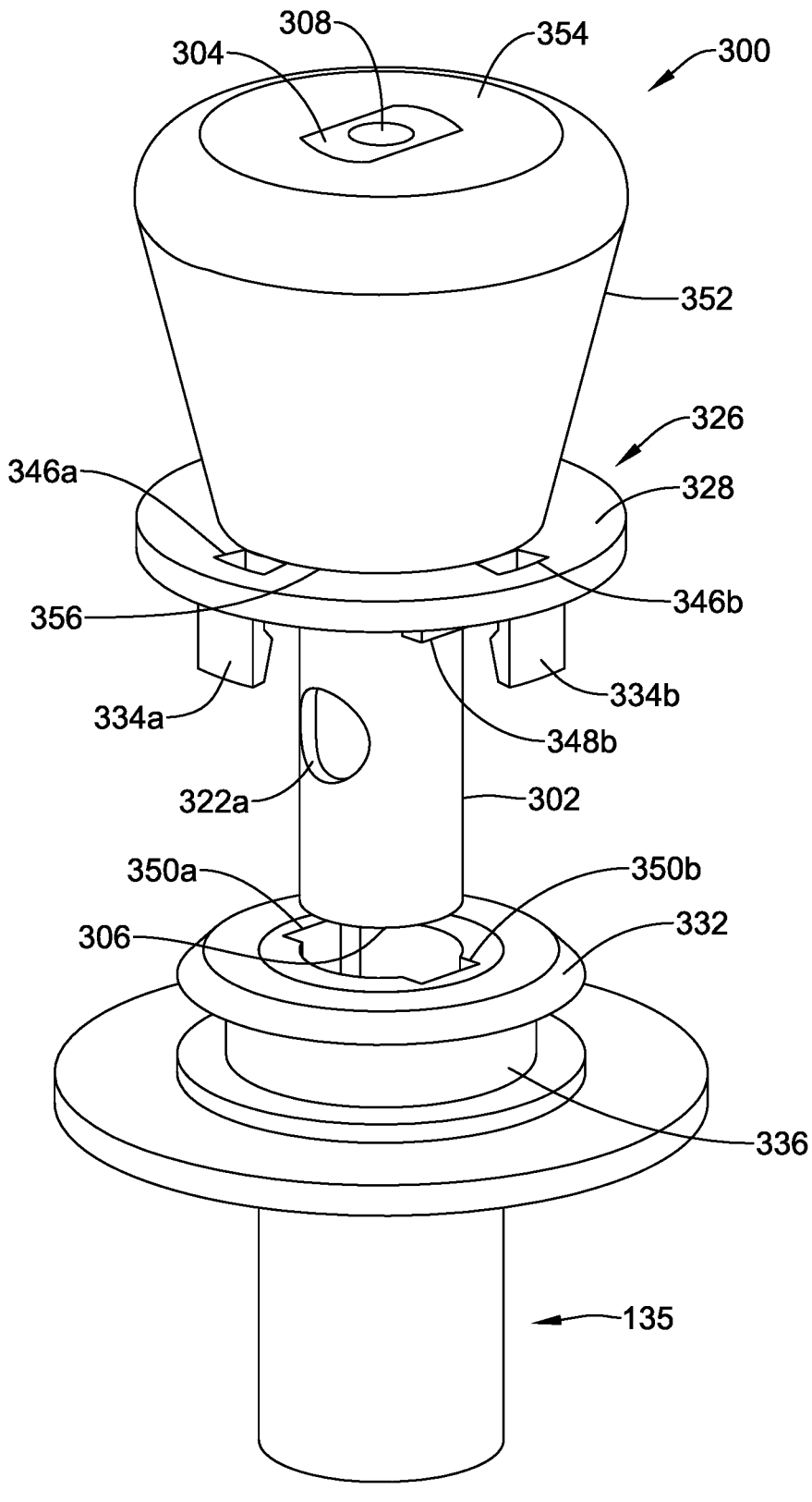
FIG. 6 depicts a partially exploded perspective view of the illustrative suction valve with a valve well.
Figure 7:
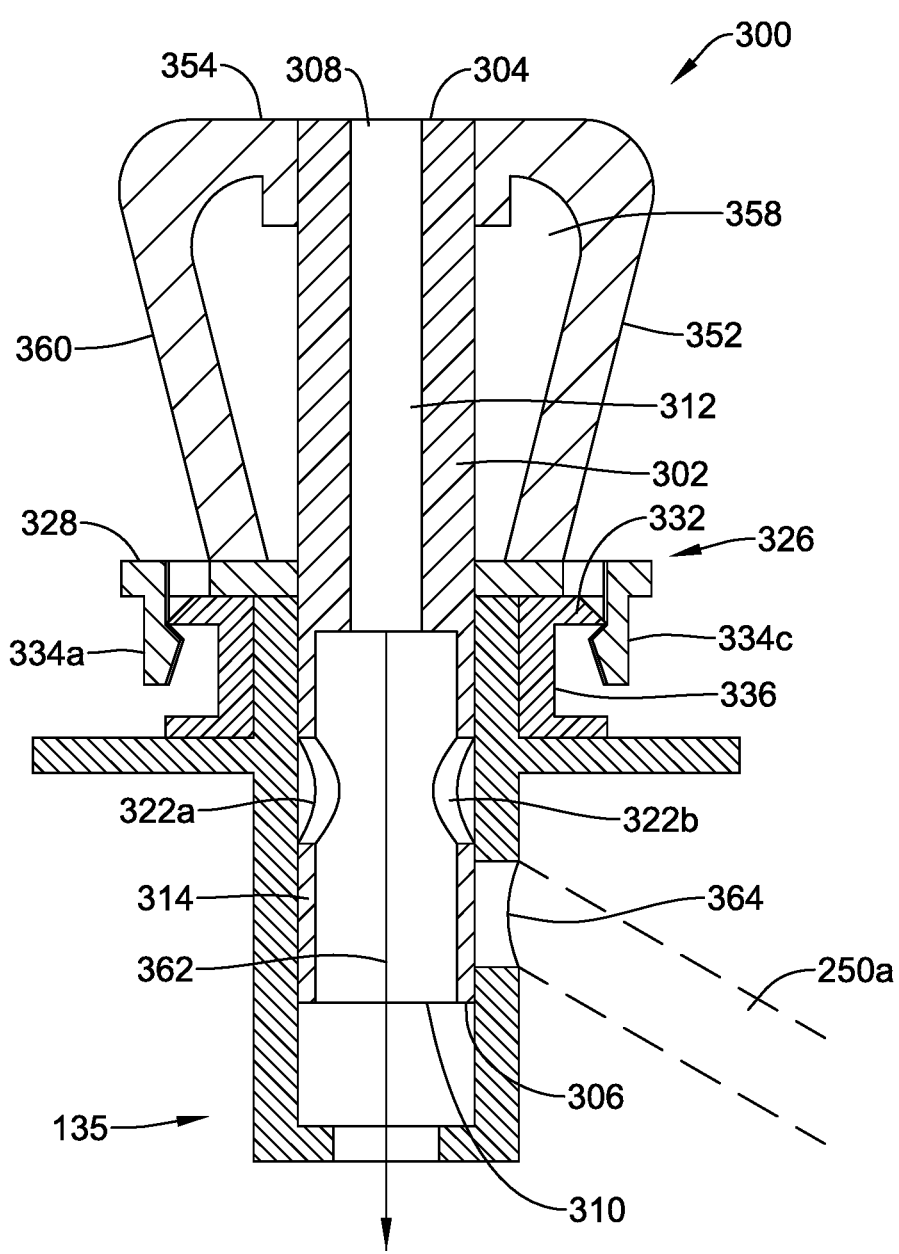
FIG. 7 depicts a schematic cross-sectional view of the illustrative suction valve of FIG. 3 assembled with a valve well and in a rest state or configuration.
Figure 8:
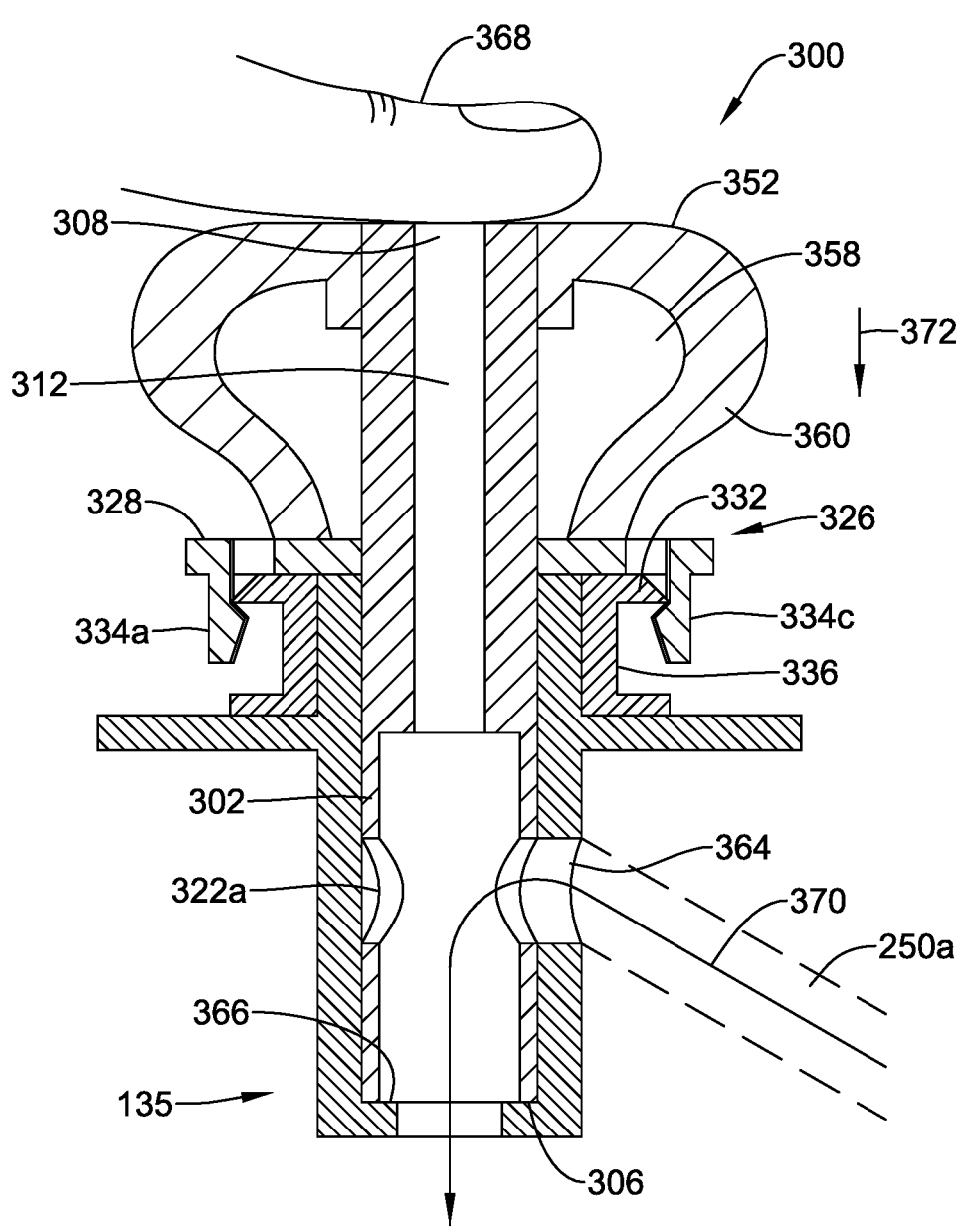
FIG. 8 depicts a schematic cross-sectional view of the illustrative suction valve of FIG. 3 assembled with a valve well and in an active state or use configuration.

An illustrative suction valve 300 that may be used with the endoscope 100 and system 200 described herein will be described with respect to FIGS. 3-8. FIG. 3 depicts a top perspective view of an illustrative suction valve 300. FIG. 4 depicts a cross-sectional view of the illustrative suction valve 300, taken at line 4-4 of FIG. 3. FIG. 5 depicts a bottom perspective view of the illustrative suction valve 300. FIG. 6 depicts a partially exploded perspective view of the illustrative suction valve 300 with a valve well 135. FIG. 7 depicts a schematic cross-sectional view of the illustrative suction valve 300 assembled with the valve well 135 and in a rest state or configuration. FIG. 8 depicts a schematic cross-sectional view of the illustrative suction valve 300 assembled with the valve well 135 and in an active state or use configuration.

The suction valve 300 may include an elongate shaft 302 extending from a first, or proximal, end 304 to a second, or distal, end 306. In some cases, the elongate shaft 302 may be a generally tubular member with a lumen 312 extending from a first opening 308 adjacent the first end 304 to a second opening 310 adjacent the second end 306. However, in some embodiments, the lumen 312 may extend less than an entire length of the elongate shaft 302. For example, a region of the elongate shaft 302 adjacent to the first end 304 may be free from a lumen. The elongate shaft 302 may further include an annular sidewall 314. When the lumen 312 extends along an entire length of the elongate shaft 302, the annular sidewall 314 may also extend along an entire length of the elongate shaft 302. In other embodiments, the lumen 312 and the annular sidewall 314 may extend less than an entire length of the elongate shaft 302 with the remaining portion of the elongate shaft 302 having a generally solid cross-section.

In some embodiments, an outer dimension or outer shape of the elongate shaft 302 may vary along the length thereof. For example, the elongate shaft 302 may have a generally circular cross-sectional shape adjacent to the second end 306 and a generally stadium shaped cross-sectional shape adjacent to the first end 304 as shown in FIG. 3. The stadium shape may have two generally parallel sides connected to one another at either end by a curved line. The wall thickness of the region of the elongate shaft 302 having the stadium shaped cross-section may not be uniform. For example, the wall thickness may be greater adjacent to the curved ends than a wall thickness along the parallel sides, as shown in FIG. 3. In other embodiments, the elongate shaft 302 may have a generally uniform cross-sectional shape along a length thereof. In some examples, a diameter of the lumen 312 of the elongate shaft 302 may vary along a length of the elongate shaft 302. For example, the lumen 312 may have a first diameter 316 extending from the first end 304 of the elongate shaft to an intermediate location 320 and a second diameter 318 from the intermediate location 320 to the second end 306. In some embodiments, the intermediate location 320 may be at or adjacent to a transition region between the first cross-sectional shape (e.g., stadium) and the second cross-sectional shape (e.g., circular). The second diameter 318 may be greater than the first diameter 316. However, this is not required. In some embodiments, a diameter of the lumen 312 may be generally constant or the same along a length thereof. In other examples, the first diameter 316 may be greater than the second diameter 318.

The elongate shaft 302 may further include one or more apertures 322a, 322b extending through a thickness of the sidewall 314. The one or more apertures 322a, 322b may be positioned at an axial location between the first and second ends 304, 306 of the elongate shaft 302. In some embodiments, the one or more apertures 322a, 322b may be positioned between the intermediate location 320 and the second end 306 of the elongate shaft 302. The one or more apertures 322a, 322b may be configured to selectively fluidly couple the lumen 312 of the suction valve 300 with the suction supply line 250a, as will be described in more detail herein. In the illustrated embodiment, the elongate shaft 302 includes a first aperture 322a and a second aperture 322b. However, the elongate shaft 302 may include fewer than two or more than two apertures 322a, 322b, as desired. When two or more apertures 322a, 322b are provided, the apertures 322a, 322b may be positioned at similar axial locations along a longitudinal axis 324 of the elongate shaft 302 such that when the suction valve 300 is moved from the rest state or configuration (as shown in FIGS. 3-7) to an active state or use configuration (see, for example, FIG. 8), the apertures 322a, 322b will axially align with an opening 364 of the suction supply line 250a. The first and second apertures 322a, 322b may be circumferentially spaced about 180° from one another about the longitudinal axis 324 of the elongate shaft 302. However, other circumferential spacing intervals may be used as desired. It is contemplated that the circumferential spacing interval may be depend, at least in part, on a number of apertures 322a, 322b provided and/or orientation features configured to align the aperture(s) 322a, 322b with the suction supply line 250a.

The suction valve 300 may further include a rigid base member 326. The base member 326 may be formed from a material that does not readily undergo elastic deformation. Some illustrative materials may include, but are not limited to, polypropylene, polystyrene, nylon, polycarbonate, methacrylate, other polymers, metals, metal alloys, combinations thereof, etc. Generally, the base member 326 may have a generally planar platform region 328 having circular outer shape with a central hole 330 (see, for example, FIG. 4) extending through a thickness of the platform region 328. The central hole 330 may be sized and shaped to slidably receive the elongate shaft 302 therethrough. While the platform region 328 is shown and described as having a generally circular outer shape, the platform region 328 may take other shapes as desired, such as, but not limited to, square, rectangular, polygonal, oblong, etc. It is contemplated that the shape of the platform region 328 may be determined, at least in part, by the shape of the valve well 135. For example, the shape of the platform region 328 may be similar to the shape of the valve well 135 to allow the base member 326 to rest on a flange 332 (see, for example, FIGS. 7 and 8) of the valve well 135. Similarly, the central hole 330 may have a generally stadium shaped cross-sectional shape similar to the stadium shape of the elongate shaft 302 disposed therein. However, the central hole 330 may take other cross-sectional shapes as desired, such as, but not limited to, circular, square, rectangular, polygonal, oblong, etc. It is contemplated that the shape of the central hole 330 may be determined, at least in part, by the outer shape of the region of the elongate shaft 302 disposed therein. The platform region 328 may extend radially outward from an outer surface of the elongate shaft 302. However, the platform region 328 and/or the base member 326 may be free from attachment to the outer surface of the elongate shaft 302 such that the elongate shaft 302 may be axially displaced along its longitudinal axis 324 while the base member 326 may be axially displaced to a lesser extent, or not at all.

The base member 326 may include one or more fastening members 334a-d configured to engage a flange 332 (see, for example, FIGS. 7 and 8) extending from a collar 336 of the valve well 135. In some embodiments, the fastening members 334a-d may be formed as a monolithic structure with the base member 326. In other embodiments, the fastening members 334a-d may be formed as separate structures from the base member 326 and subsequently attached thereto. The fastening members 334a-d may include an arm portion 338a-d extending from a second side 344 of the platform region 328 of the base member 326. The arm portions 338a-d may extend at an angle generally orthogonal to the platform region 328. However, this is not required. The arm portions 338a-d may extend at non-orthogonal angles, as desired. The arm portions 338a-d may each include a radially extending protrusion 340a-d. The sides of the arm portions 338a-d may include angles or slopes such that the protrusions 340a-d form a peak. The protrusions 340a-d may be configured engage a lower surface of the flange 332 while the sloped surfaces facilitate assembly and disassembly of the fastening members 334a-d with the flange 332. In some cases, the fastening members 334a-d may be clips configured to form a snap fit with the flange 332 of the valve well 135. For example, a second side 344 of the base member 326 may rest against an upper surface of the flange 332 while the fastening members 334a-d are configured to engage a lower surface of the flange 332.

The arm portions 338a-d of the fastening members 334a-d may flex or bend to allow the fastening members 334a-d to engage the flange 332. Apertures 346a-d may be formed in the platform region 328 of the base member 326 adjacent to the fastening members 334a-d to facilitate flexing or being of the arm portions 338a-d. However, this is not required. While the base member 326 is illustrated as including four fastening members 334a-d, the base member 326 may include fewer than four or more than four fastening members 334a-d, as desired. In the illustrated embodiment, the fastening members 334a-d are circumferentially spaced from one another by about 90°. However, this is not required. The fastening members 334a-d may be arranged in any uniform or non-uniform arrangement about a circumference of the base member 326. It is further contemplated that the fastening members 334a-d may be configured to engage the flange 332 in a threaded arrangement, a friction fit, a bayonet-style locking mechanism, etc.

The base member 326 may further include one or more orientation features 348a, 348b configured to align with mating orientation features 350a, 350b (see, for example, FIG. 6) in the collar 336 and/or flange 332 of the valve well 135. In some examples, the orientation features 348a, 348b may be axially extending legs or protrusions. In some embodiments, the orientation features 348a, 348b may be a curved protrusion configured to mate with a recess 350a, 350b formed in the curved wall of the collar 336, although this is not required. The orientation features 348a, 348b may extend at a generally orthogonal angle to the platform region 328 of the base member 326 or parallel to the longitudinal axis of the 324 of the elongate shaft 302. However, this is not required. The orientation features 348a, 348b may be sized, shaped, and oriented to align and mate with the corresponding features (e.g., recesses 350a, 350b) on the flange 332. While the base member 326 is illustrated as including a first and a second orientation feature 348a, 348b, the base member 326 may include fewer than two or more than two orientation features 348a, 348b, as desired. The orientation features 348a, 348b may be arranged in any uniform or non-uniform arrangement about a circumference of the base member 326. In the illustrated embodiment, the orientation features 348a, 348b are circumferentially spaced from one another by about 180°. However, this is not required. During assembly of the suction valve 300 with the valve well 135, the orientation features 348a, 348b may be aligned with mating recesses or slots 350a, 350b in the collar 336 of the valve well 135. The orientation features 348a, 348b and the mating slots 350a, 350b of the collar 336 may be positioned such that when the suction valve 300 is positioned within the valve well 135, at least one of the apertures 322a, 322b will align with the opening of the suction supply line 250a when the suction valve 300 is actuated to the active state or use configuration. In some examples, the orientation features 348a, 348b may be circumferentially aligned with the apertures 322a, 322b. In other examples, the orientation features 348a, 348b may be circumferentially offset from the apertures 322a, 322b, as illustrated in FIG. 6.

In some embodiments, the orientation features 348a, 348b may be combined with the fastening members 334a-d. For example, the suction valve 300 may be provided with one or more radially extending protrusions configured to mate with one or more "J" shaped slots in the collar 336 to form a bayonet style locking mechanism which both releasably secures the suction valve 300 to the valve well 135 as well as maintains proper orientation between the valve well 135 and the apertures 322a, 322b in the elongate shaft 302. The reverse configuration is also contemplated in which one or more "J" shaped slots are formed in the suction valve 300 and one or more protrusions extend from the collar 336 or flange 332. This is just one example. Other coupling mechanisms may be used, as desired.

The suction valve 300 may further include an actuation cap or compliant member 352 configured to flex or deform in response to a user input. The compliant member 352 may extend from a first end 354 adjacent to the first end 304 of the elongate shaft 302 to a second end 356 adjacent to a first or upper side 342 of the base member 326. The compliant member 352 may be fixedly coupled to the outer surface of the elongate shaft 302 adjacent the first end 304 of the elongate shaft 302 or along a portion of the length of the elongate shaft 302 extending between the base member 326 and the first end 304 of the elongate shaft 302. It is contemplated that the compliant member 352 may not cover the first opening 308 at the first end 304 of the elongate shaft 302 to allow for a vent path when the suction valve 300 is in the rest state. The compliant member 352 may also be fixedly coupled to the first side 342 of the base member 326. In some cases, the base member 326 may extend radially beyond the second end 356 of compliant member 352 such that the base member 326 has a greater diameter than the second end 356 of the compliant member 352. However, this is not required. In some embodiments, the compliant member 352 may be overmolded with the elongate shaft 302 and the base member 326. However, other coupling techniques may be used, as desired.

The compliant member 352 may be formed from a material that allows the compliant member 352 to undergo elastic deformation in response to an applied force and return to a rest or original configuration in the absence of the applied force. The compliant member 352 may be formed from silicones, polyurethanes, or other soft durometer elastomers, rubbers or polymers. The cross-sectional dimension of the compliant member 352 may decrease from the first end 354 to the second end 356 thereof. In some examples, the compliant member 352 may take the shape of an inverted truncated cone. However, this is not required. In other examples, the compliant member 352 may have a generally hemispherical or dome-like shape in the rest configuration. The compliant member 352 may take yet other shapes, as desired, including, but not limited to, cylindrical, rectangular prism, cubic, ovular, etc. It is further contemplated that the compliant member 352 may be generally solid, partially solid, or may define an open cavity 358 therein.

FIG. 7 depicts a schematic cross-section of the illustrative suction valve 300 of FIG. 3 positioned within a valve well 135 and in a rest state or configuration. For clarity, the valve well 135 is shown without the remaining portion of the endoscope handle 115. As described above, in the rest state, suction is not applied to the working channel 235 of the endoscope 100. Instead, the suction pump (not explicitly shown) draws air from the atmosphere via the lumen 312 of the elongate shaft 302. To assemble the suction valve 300 with the valve well 135, the second end 306 of the elongate shaft 302 is inserted into the valve well 135. The suction valve 300 may be rotated as necessary to align the orientation features 348a, 348b of the suction valve 300 with the mating slots 350a, 350b in the collar 336 of the valve well 135. As the illustrated suction valve 300 includes two orientation features 348a, 348b circumferentially offset from one another by about 180° and each offset from the apertures 322a, 322b by about 90°, the suction valve 300 may be assembled with either the first aperture 322a or the second aperture 322b aligned with the suction supply line 250a. While not explicitly shown, the suction valve 300 may include visual indicia to facilitate assembly of the suction valve with the valve well 135. The elongate shaft 302 may be advanced into the valve well 135 until the second side 344 of the base member 326 contacts an upper surface of the flange 332. The downward movement of the suction valve 300 may allow the fastening members 334a-d to form a snap fit with or otherwise engage the flange 332 to prevent unintentional disengagement of the suction valve 300 from the valve well 135. However, the suction valve 300 may be removed from the valve well 135 with an applied force. For example, with sufficient upward force, the arm portions 338a-d may deflect radially outward to allow the suction valve 300 to be disassembled from the valve well 135.

In the rest configuration, as shown in FIG. 7, the apertures 322a, 322b are axially offset from the suction supply line 250a and the first opening 308 adjacent the first end 304 of the elongate shaft 302 is open or unblocked. The suction pump (not explicitly shown) draws air from the atmosphere via the lumen 312 of the elongate shaft 302, as shown at arrow 362. In some cases, air may also be drawn in via a gap between the second side 344 of the base member 326 and the surface of the flange 332. The sidewall 314 of the elongate shaft 302 blocks the opening 364 of the suction supply line 250a and precludes suction from being applied to the suction supply line 250a.

FIG. 8 depicts a schematic cross-section of the illustrative suction valve 300 of FIG. 3 positioned within a valve well 135 and in an active state or use configuration. When suction within the working channel 235 is desired, the user may block the first opening 308 at the first end 304 of the elongate shaft 302 with, for example, a thumb or finger 368. In addition to blocking the first opening 308, the user may exert a downward or distal force, as shown at arrow 372 on the suction valve 300 to move the elongate shaft 302 axially along or parallel to the longitudinal axis 324 of the elongate shaft 302 within the valve well 135. As the elongate shaft 302 is axially displaced, the sidewall 360 of the compliant member 352 may deform to allow the elongate shaft 302 to move. For example, the sidewall 360 may deform radially outward. This is just one example. The sidewalls may deform in other manners. The elongate shaft 302 may be distally displaced within the valve well 135 to align at least one of the apertures 322a, 322b in the elongate shaft 302 with the opening 364 of the suction supply line 250a. In the illustrated embodiment, the second aperture 322b is aligned with the opening 364 of the suction supply line 250a to fluidly couple the suction pump with the suction supply line 250a and ultimately the working channel 235. However, as noted above, in some cases, the first aperture 322a may be aligned with the opening 364 of the suction supply line 250a. The base member 326 may be displaced downward into the flange 332 to the extent that there is a gap between the second side 344 of the base member 326 and the flange 332 prior to actuation of the elongate shaft 302. The base member 326 may not form a fluid-tight or gas-tight seal with the surface of the flange 332. However, air leaks at this base member 326/flange 332 interface may be negligible and not interfere with the ability of the suction pump to draw fluid or debris from the working channel 235. It is contemplated that the second side 344 of the base member 326 may include a gasket, O-ring, or other sealing member secured thereto to create a tighter seal between the second side 344 of the base member 326 and the surface of the flange 332.

It is contemplated that the apertures 322a, 322b may be located at an axial location along the elongate shaft 302 that allows at least one of the apertures 322a, 322b to be aligned with the opening 364 of the suction supply line 250a when the second end 306 of the elongate shaft 302 engages a flange 366 within the valve well 135. For example, the user may depress the first end 304 of the elongate shaft 302 until the second end 306 engages the radially inwardly extending flange 366. This may create a mechanical stop that indicates to the user the suction valve 300 is in the active state. In the active state or use configuration, as shown in FIG. 8, at least one of the apertures 322a, 322b (e.g., the second aperture 322b in the illustrated embodiment) is axially aligned with the opening 364 of the suction supply line 250a and the first opening 308 at the first end 304 of the elongate shaft 302 is blocked or closed (e.g., by the user's finger 368). The user's finger 368 may prevent the suction pump from drawing air from atmosphere. The suction pump (not explicitly shown) draws air from the suction supply line 250a (which is fluidly coupled to the working channel 235), as shown at arrow 370. This allows fluid or debris to be removed from the working channel 235 via the suction force from the suction pump. When the suction procedure is complete, the user may simply remove their finger 368 from the suction valve 300. The compliant member 352 may spring back or automatically return to the rest state with the apertures 322a, 322b and the opening 364 of the suction supply line 250a becomes misaligned, as shown in FIG. 7, without the use of a spring. It is contemplated that a change in diameter or shape of the elongate shaft 302 may create a mechanical stop between the elongate shaft 302 and the rigid base 326 as the suction valve 300 is returning to the rest configuration.

Figure 9:
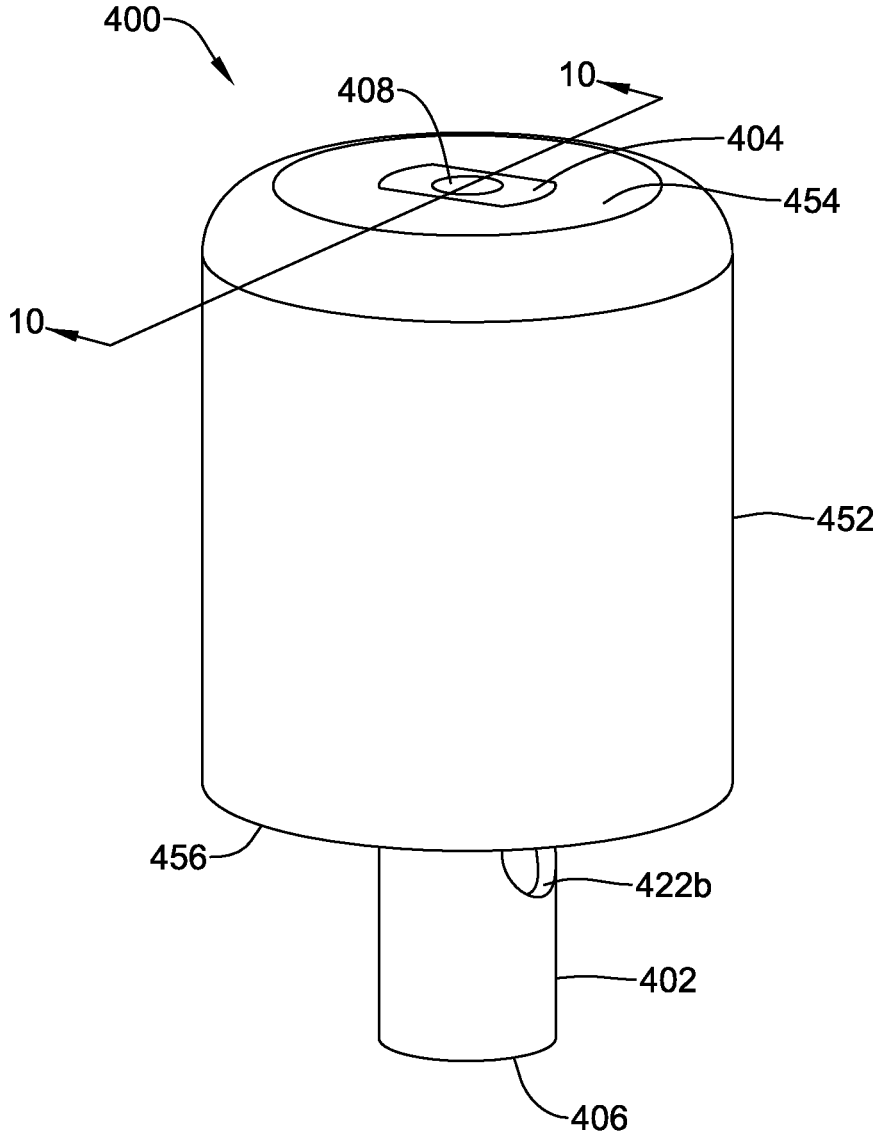
FIG. 9 depicts a top perspective view of an illustrative suction valve.
Figure 10:
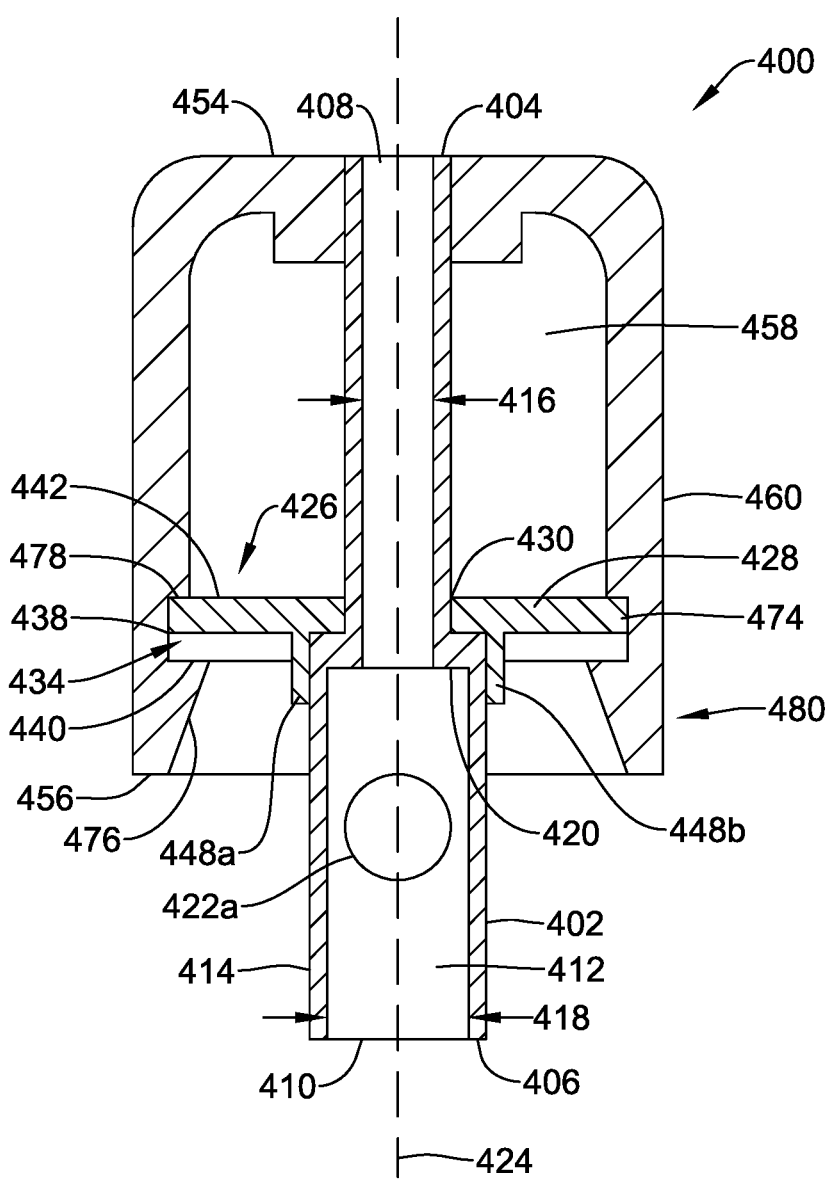
FIG. 10 depicts a cross-sectional view of the illustrative suction valve of FIG. 9, taken at line 10-10 of FIG. 9.
Figure 11:
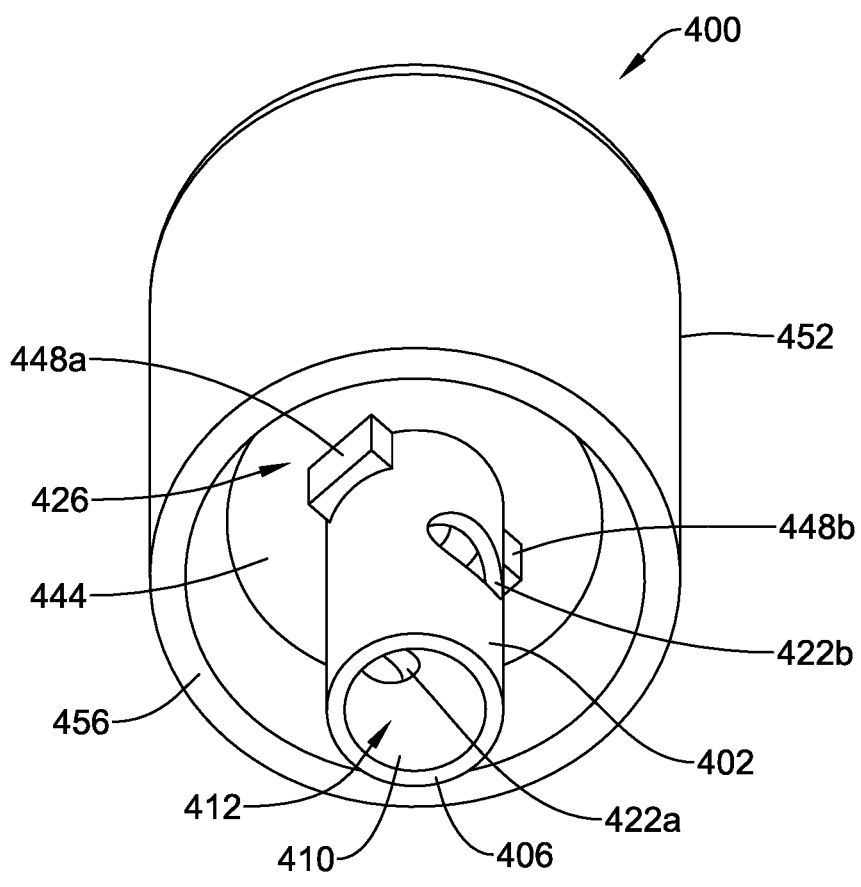
FIG. 11 depicts a bottom perspective view of the illustrative suction valve of FIG. 9.
Figure 12:
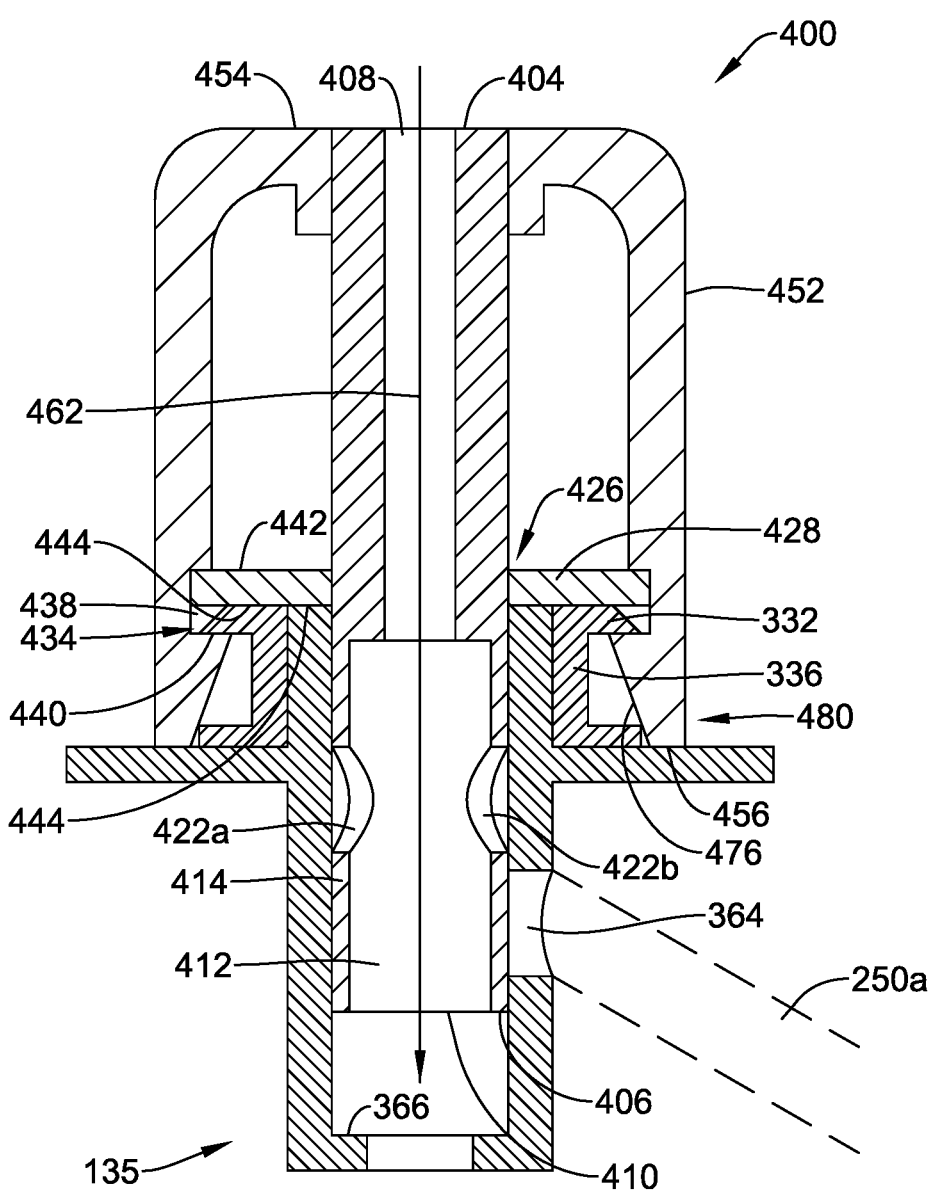
FIG. 12 depicts a schematic cross-sectional view of the illustrative suction valve of FIG. 9 assembled with a valve well and in a rest state or configuration.
Figure 13:
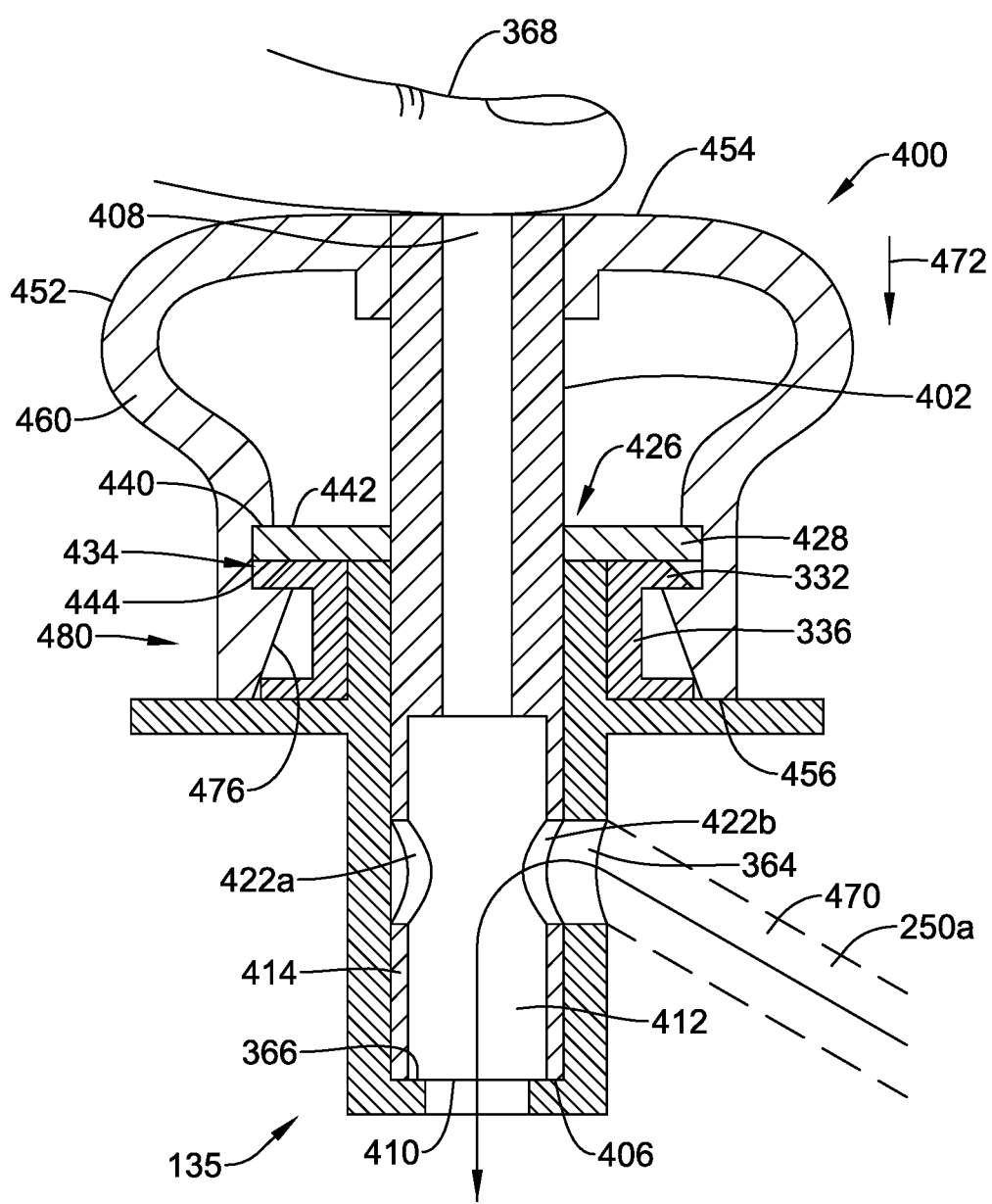
FIG. 13 depicts a schematic cross-sectional view of the illustrative suction valve of FIG. 9 assembled with a valve well and in an active state or use configuration.

Another illustrative suction valve 400 that may be used with the endoscope 100 and system 200 described herein will be described with respect to FIGS. 9-13. FIG. 9 depicts a top perspective view of an illustrative suction valve 400. FIG. 10 depicts a cross-sectional view of the illustrative suction valve 400, taken at line 10-10 of FIG. 9. FIG. 11 depicts a bottom perspective view of the illustrative suction valve 400. FIG. 12 depicts a schematic cross-sectional view of the illustrative suction valve 400 assembled with the valve well 135 and in a rest state or configuration. FIG. 13 depicts a schematic cross-sectional view of the illustrative suction valve 400 assembled with the valve well 135 and in an active state or use configuration.

The suction valve 400 may include an elongate shaft 402 extending from a first, or proximal, end 404 to a second, or distal, end 406. In some cases, the elongate shaft 402 may be a generally tubular member with a lumen 412 extending from a first opening 408 adjacent the first end 404 to a second opening 410 adjacent the second end 406. However, in some embodiments, the lumen 412 may extend less than an entire length of the elongate shaft 402. For example, a region of the elongate shaft 402 adjacent to the first end 404 may be free from a lumen. The elongate shaft 402 may further include an annular sidewall 414. When the lumen 412 extends along an entire length of the elongate shaft 402, the annular sidewall 414 may also extend along an entire length of the elongate shaft 402. In other embodiments, the lumen 412 and the annular sidewall 414 may extend less than an entire length of the elongate shaft 402 with the remaining portion of the elongate shaft 402 having a generally solid cross-section.

In some embodiments, an outer dimension or outer shape of the elongate shaft 402 may vary along the length thereof. For example, the elongate shaft 402 may have a generally circular cross-sectional shape adjacent to the second end 406 and a generally stadium shaped cross-sectional shape adjacent to the first end 404 as shown in FIG. 9. The stadium shape may have two generally parallel sides connected to one another at either end by a curved line. The wall thickness of the region of the elongate shaft 402 having the stadium shaped cross-section may not be uniform. For example, the wall thickness may be greater adjacent to the curved ends than a wall thickness along the parallel sides, as shown in FIG. 9. In other embodiments, the elongate shaft 402 may have a generally uniform cross-sectional shape along a length thereof. In some examples, a diameter of the lumen 412 of the elongate shaft 402 may vary along a length of the elongate shaft 402. For example, the lumen 412 may have a first diameter 416 extending from the first end 404 of the elongate shaft to an intermediate location 420 and a second diameter 418 from the intermediate location 420 to the second end 406. In some embodiments, the intermediate location 420 may be at or adjacent to a transition region between the first cross-sectional shape (e.g., stadium) and the second cross-sectional shape (e.g., circular). The second diameter 418 may be greater than the first diameter 416. However, this is not required. In some embodiments, a diameter of the lumen 412 may be generally constant or the same along a length thereof. In other examples, the first diameter 416 may be greater than the second diameter 418.

The elongate shaft 402 may further include one or more apertures 422a, 422b extending through a thickness of the sidewall 414. The one or more apertures 422a, 422b may be positioned at an axial location between the first and second ends 404, 406 of the elongate shaft 402. In some embodiments, the one or more apertures 422a, 422b may be positioned between the intermediate location 420 and the second end 406 of the elongate shaft 402. The one or more apertures 422a, 422b may be configured to selectively fluidly couple the lumen 412 of the suction valve 400 with the suction supply line 250a, as will be described in more detail herein. In the illustrated embodiment, the elongate shaft 402 includes a first aperture 422a and a second aperture 422b. However, the elongate shaft 402 may include fewer than two or more than two apertures 422a, 422b, as desired. When two or more apertures 422a, 422b are provided, apertures 422a, 422b may be positioned at similar axial locations along a longitudinal axis 424 of the elongate shaft 402 such that when the suction valve 400 is moved from the rest state or configuration (as shown in FIGS. 9-12) to an active state or use configuration (see, for example, FIG. 13), the apertures 422a, 422b will axially align with an opening 364 of the suction supply line 250a. The first and second apertures 422a, 422b may be circumferentially spaced about 180° from one another about the longitudinal axis 424 of the elongate shaft 402. However, other circumferential spacing intervals may be used as desired. It is contemplated that the circumferential spacing interval may be depend, at least in part, on a number of apertures 422a, 422b provided and/or orientation features configured to align the aperture(s) 422a, 422b with the suction supply line 250a.

The suction valve 400 may further include a rigid base member 426. The base member 426 may be formed from a material that does not readily undergo elastic deformation. Some illustrative materials may include, but are not limited to, polypropylene, polystyrene, nylon, polycarbonate, methacrylate, other polymers, metals, metal alloys, combinations thereof, etc. Generally, the base member 426 may have a generally planar platform region 428 having circular outer shape with a central hole 430 (see, for example, FIG. 10) extending through a thickness of the platform region 428. The central hole 430 may be sized and shaped to slidably receive the elongate shaft 402 therethrough. While the platform region 428 is shown and described as having a generally circular outer shape, the platform region 428 may take other shapes as desired, such as, but not limited to, square, rectangular, polygonal, oblong, etc. It is contemplated that the shape of the platform region 428 may be determined, at least in part, by the shape of the valve well 135. For example, the shape of the platform region 428 may be similar to the shape of the valve well 135 to allow the base member 426 to rest on a flange 332 (see, for example, FIGS. 12 and 13) of the valve well 135. Similarly, the central hole 430 may have a generally stadium shaped cross-sectional shape similar to the stadium shape of the elongate shaft 402 disposed therein. However, the central hole 430 may take other cross-sectional shapes as desired, such as, but not limited to, circular, square, rectangular, polygonal, oblong, etc. It is contemplated that the shape of the central hole 430 may be determined, at least in part, by the outer shape of the region of the elongate shaft 402 disposed therein. The platform region 428 may extend radially outward from an outer surface of the elongate shaft 402. However, the platform region 428 and/or the base member 426 may be free from attachment to the outer surface of the elongate shaft 402 such that the elongate shaft 402 may be axially displaced along its longitudinal axis 424 while the base member 426 may be axially displaced to a lesser extent, or not at all.

The base member 426 may further include one or more orientation features 448a, 448b configured to align with mating orientation features 350a, 350b (see, for example, FIG. 6) in the collar 336 and/or flange 332 of the valve well 135. In some examples, the orientation features 448a, 448b may be axially extending legs or protrusions. In some embodiments, the orientation features 448a, 448b may be a curved protrusion configured to mate with a recess 350a, 350b formed in the curved wall of the collar 336, although this is not required. The orientation features 448a, 448b may extend at a generally orthogonal angle to the platform region 428 of the base member 426 or parallel to the longitudinal axis of the 424 of the elongate shaft 402. However, this is not required. The orientation features 448a, 448b may be sized, shaped, and oriented to align and mate with the corresponding features (e.g., recesses 350a, 350b) on the flange 332. While the base member 426 is illustrated as including a first and a second orientation feature 448a, 448b, the base member 426 may include fewer than two or more than two orientation features 448a, 448b, as desired. The orientation features 448a, 448b may be arranged in any uniform or non-uniform arrangement about a circumference of the base member 426. In the illustrated embodiment, the orientation features 448a, 448b are circumferentially spaced from one another by about 180°. However, this is not required. During assembly of the suction valve 400 with the valve well 135, the orientation features 448a, 448b may be aligned with mating recesses or slots 350a, 350b in the collar 336 of the valve well 135. The orientation features 448a, 448b and the mating slots 350a, 350b of the collar 336 may be positioned such that when the suction valve 400 is positioned within the valve well 135, at least one of the apertures 422a, 422b will align with the opening of the suction supply line 250a when the suction valve 400 is actuated to the active state or use configuration. In some examples, the orientation features 448a, 448b may be circumferentially aligned with the apertures 422a, 422b. In other examples, the orientation features 448a, 448b may be circumferentially offset from the apertures 422a, 422b, as illustrated in FIG. 10.

The suction valve 400 may further include an actuation cap or compliant member 452 configured to flex or deform in response to a user input. The compliant member 452 may extend from a first end 454 adjacent to the first end 404 of the elongate shaft 402 to a second end 456 extending distally of the base member 426. The compliant member 452 may be fixedly coupled to the outer surface of the elongate shaft 402 adjacent the first end 404 of the elongate shaft 402 or along a portion of the length of the elongate shaft 402 extending between the base member 426 and the first end 404 of the elongate shaft 402. It is contemplated that the compliant member 452 may not cover the first opening 408 at the first end 404 of the elongate shaft 402 to allow for a vent path when the suction valve 400 is in the rest state. The compliant member 452 may also be fixedly coupled to the first side 442 and/or an outer perimeter 474 of the base member 426. In some cases, the compliant member 452 may extend radially beyond the outer perimeter 474 of the base member such that the compliant member 452 has a greater diameter than the base member 426. However, this is not required. In some embodiments, the compliant member 452 may be overmolded with the elongate shaft 402 and the base member 426. However, other coupling techniques may be used, as desired.

The compliant member 452 may be formed from a material that allows the compliant member 452 to undergo elastic deformation in response to an applied force and return to a rest or original configuration in the absence of the applied force. The compliant member 452 may be formed from silicones, polyurethanes, or other soft durometer elastomers, rubbers or polymers. The cross-sectional dimension of the compliant member 452 may be substantially uniform from the first end 454 to the second end 456 thereof. In some examples, the compliant member 452 may take the shape of a cylinder. However, this is not required. For example, the outer diameter of the compliant member 452 may increase and/or decrease along the length thereof. In other examples, the compliant member 452 may have a generally hemispherical or dome-like shape in the rest configuration. The compliant member 452 may take yet other shapes, as desired, including, but not limited to, a truncated cone, rectangular prism, cubic, ovular, etc. It is further contemplated that the compliant member 452 may be generally solid, partially solid, or may define an open cavity 458 therein.

FIG. 12 depicts a schematic cross-section of the illustrative suction valve 400 of FIG. 9 positioned within a valve well 135 and in a rest state or configuration. For clarity, the valve well 135 is shown without the remaining portion of the endoscope handle 115. As described above, in the rest state, suction is not applied to the working channel 235 of the endoscope 100. Instead, the suction pump (not explicitly shown) draws air from the atmosphere via the lumen 412 of the elongate shaft 402. To assemble the suction valve 400 with the valve well 135, the second end 406 of the elongate shaft 402 is inserted into the valve well 135. The suction valve 400 may be rotated as necessary to align the orientation features 448a, 448b of the suction valve 400 with the mating slots 350a, 350b in the collar 336 of the valve well 135. As the illustrated suction valve 400 includes two orientation features 448a, 448b circumferentially offset from one another by about 180° and each offset from the apertures 422a, 422b by about 90°, the suction valve 400 may be assembled with either the first aperture 422a or the second aperture 422b aligned with the suction supply line 250a. While not explicitly shown, the suction valve 400 may include visual indicia to facilitate assembly of the suction valve with the valve well 135. The elongate shaft 402 may be advanced into the valve well 135 until the second side 444 of the base member 426 contacts an upper surface of the flange 332. The downward movement of the suction valve 400 may allow the fastening members 434 to form a snap fit with or otherwise engage the flange 332 to prevent unintentional disengagement of the suction valve 400 from the valve well 135. However, the suction valve 400 may be removed from the valve well 135 with an applied force. For example, with sufficient upward force, the arm portions 338a-d may deflect radially outward to allow the suction valve 400 to be disassembled from the valve well 135.

The compliant member 452 may include a fastening member 434 configured to engage a flange 332 (see, for example, FIGS. 12 and 13) extending from a collar 336 of the valve well 135. In some embodiments, the fastening member 434 may be formed as a monolithic structure with the compliant member 452. However, this is not required.

The fastening member 434 may include an annular recess 438 formed in an inner surface of the sidewall 460 of the compliant member 452. The recess 438 may be defined by an area of reduced thickness of the sidewall 460 of the compliant member 452. A bottom surface 440 of the recess 438 may be configured to engage a lower surface of the flange 332 while a top surface 478 of the recess 438 may rest upon the first surface 442 of the base member 426. A second end region 480 of the compliant member 452 may flex radially outward to allow the fastening member 434 to engage the flange 332 in a snap fit manner. In some embodiments, the bottom surface 440 of the recess 438 may extend radially inwards to reduce an inner diameter of the compliant member 452 to allow the fastening member 434 to engage the flange 332. An inner surface 476 of the compliant member adjacent the second end region 480 thereof may be sloped or angled such that the second end 456 of the compliant member 452 has a reduced wall thickness to allow the second end 456 to fit over the collar 336 of the valve well 135.

In the rest configuration, as shown in FIG. 12, the apertures 422a, 422b are axially offset from the suction supply line 250a and the first opening 408 adjacent the first end 404 of the elongate shaft 402 is open or unblocked. The suction pump (not explicitly shown) draws air from the atmosphere via the lumen 412 of the elongate shaft 402, as shown at arrow 462. In some cases, air may also be drawn in via a gap between the second side 444 of the base member 426 and the surface of the flange 332. The sidewall 414 of the elongate shaft 402 blocks the opening 364 of the suction supply line 250a and precludes suction from being applied to the suction supply line 250a.

FIG. 13 depicts a schematic cross-section of the illustrative suction valve 400 of FIG. 9 positioned within a valve well 135 and in an active state or use configuration. When suction within the working channel 235 is desired, the user may block the first opening 408 at the first end 404 of the elongate shaft 402 with, for example, a thumb or finger 368. In addition to blocking the first opening 408, the user may exert a downward or distal force, as shown at arrow 472 on the suction valve 400 to move the elongate shaft 402 axially along or parallel to the longitudinal axis 424 of the elongate shaft 402 within the valve well 135. As the elongate shaft 402 is axially displaced, the sidewall 460 of the compliant member 452 may deform to allow the elongate shaft 402 to move. For example, the sidewall 460 may deform radially outward. This is just one example. The sidewalls may deform in other manners. The elongate shaft 402 may be distally displaced within the valve well 135 to align at least one of the apertures 422a, 422b in the elongate shaft 402 with the opening 364 of the suction supply line 250a. In the illustrated embodiment, the second aperture 422b is aligned with the opening 364 of the suction supply line 250a to fluidly couple the suction pump with the suction supply line 250a and ultimately the working channel 235. However, as noted above, in some cases, the first aperture 422a may be aligned with the opening 364 of the suction supply line 250a. The base member 426 may be displaced downward into the flange 332 to the extent that there is a gap between the second side 444 of the base member 426 and the flange 332 prior to actuation of the elongate shaft 402. The base member 426 may not form a fluid-tight or gas-tight seal with the surface of the flange 332. However, air leaks at this base member 426/flange 332 interface may be negligible and not interfere with the ability of the suction pump to draw fluid or debris from the working channel 235. It is contemplated that the second side 444 of the base member 426 may include a gasket, O-ring, or other sealing member secured thereto to create a tighter seal between the second side 444 of the base member 426 and the surface of the flange 332.

It is contemplated that the apertures 422a, 422b may be located at an axial location along the elongate shaft 402 that allows at least one of the apertures 422a, 422b to be aligned with the opening 364 of the suction supply line 250a when the second end 406 of the elongate shaft 402 engages a flange 366 within the valve well 135. For example, the user may depress the first end 404 of the elongate shaft 402 until the second end 406 engages the radially inwardly extending flange 366. This may create a mechanical stop that indicates to the user the suction valve 400 is in the active state. In the active state or use configuration, as shown in FIG. 13, at least one of the apertures 422a, 422b (e.g., the second aperture 422b in the illustrated embodiment) is axially aligned with the opening 364 of the suction supply line 250a and the first opening 408 at the first end 404 of the elongate shaft 402 is blocked or closed (e.g., by the user's finger 368). The user's finger 368 may prevent the suction pump from drawing air from atmosphere. The suction pump (not explicitly shown) draws air from the suction supply line 250a (which is fluidly coupled to the working channel 235), as shown at arrow 470. This allows fluid or debris to be removed from the working channel 235 via the suction force from the suction pump. When the suction procedure is complete, the user may simply remove their finger 368 from the suction valve 400. The compliant member 452 may spring back or automatically return to the rest state with the apertures 422a, 422b and the opening 364 of the suction supply line 250a becomes misaligned, as shown in FIG. 12, without the use of a spring. It is contemplated that a change in diameter or shape of the elongate shaft 402 may create a mechanical stop between the elongate shaft 402 and the rigid base 426 as the suction valve 400 is returning to the rest configuration.

Figure 14:
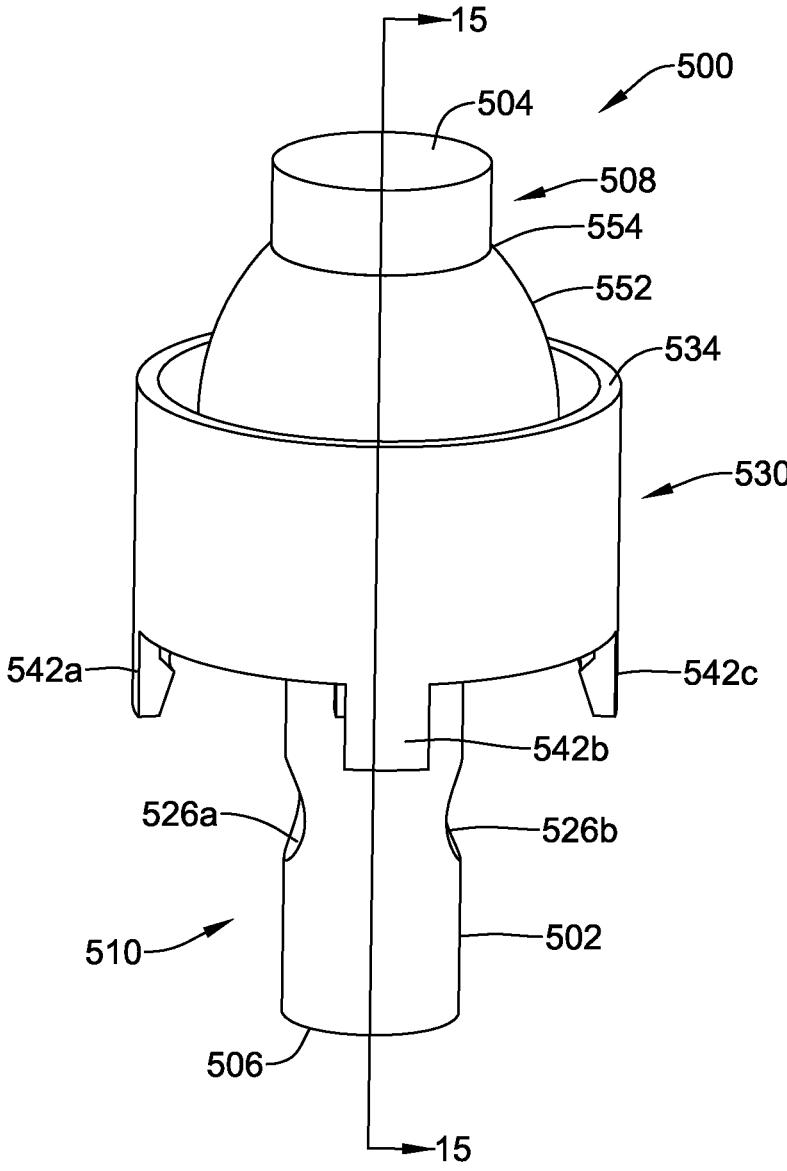
FIG. 14 depicts a top perspective view of another illustrative suction valve.
Figure 15:
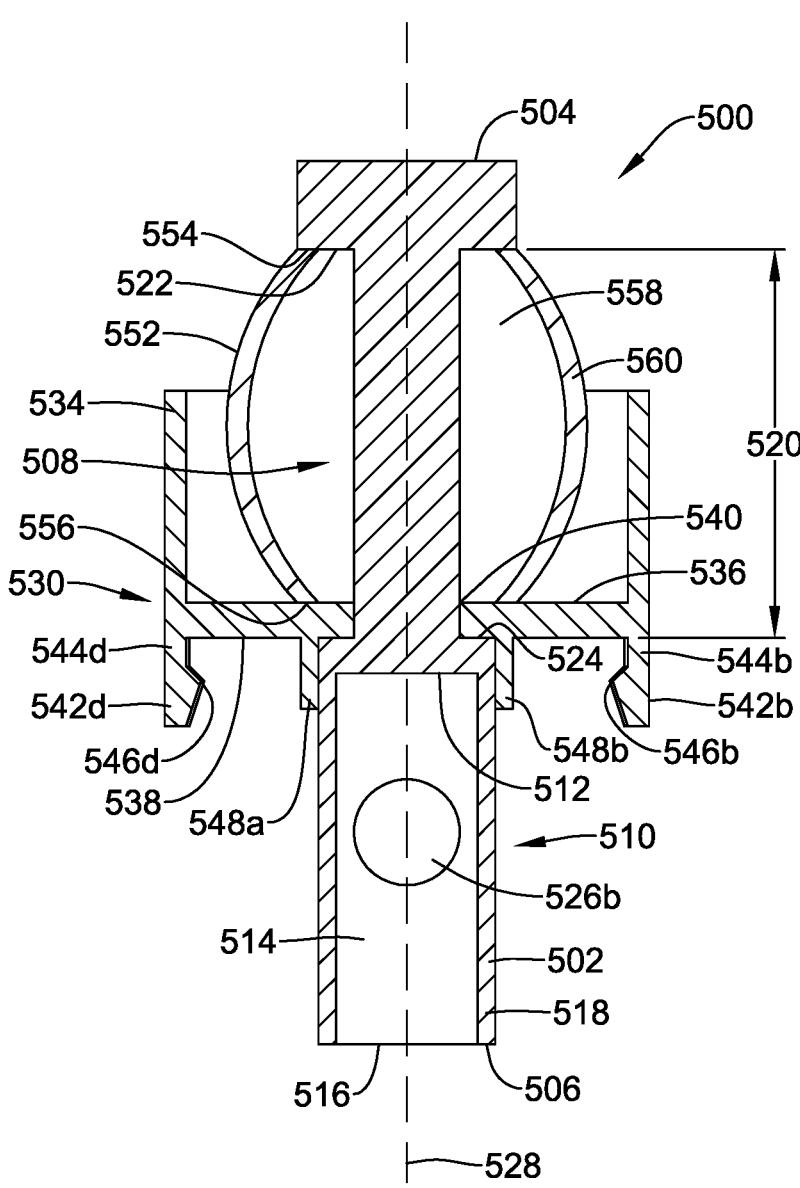
FIG. 15 depicts a cross-sectional view of the illustrative suction valve of FIG. 14, taken at line 15-15 of FIG. 14.
Figure 16:
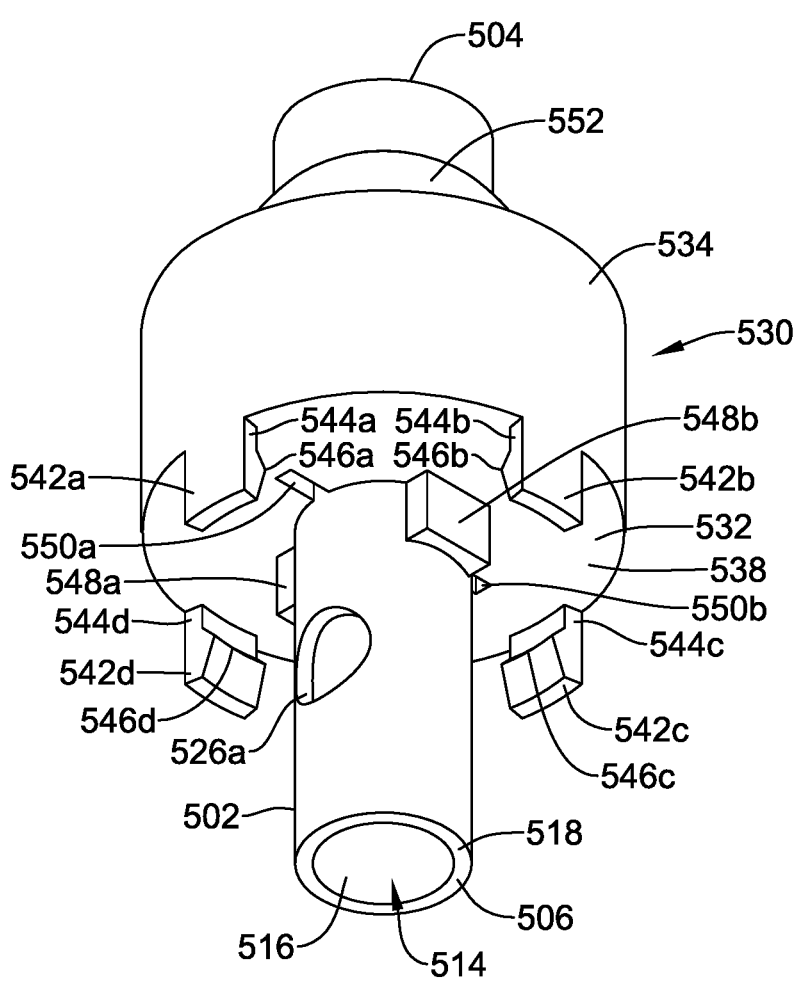
FIG. 16 depicts a bottom perspective view of the illustrative suction valve of FIG. 14.
Figure 17:
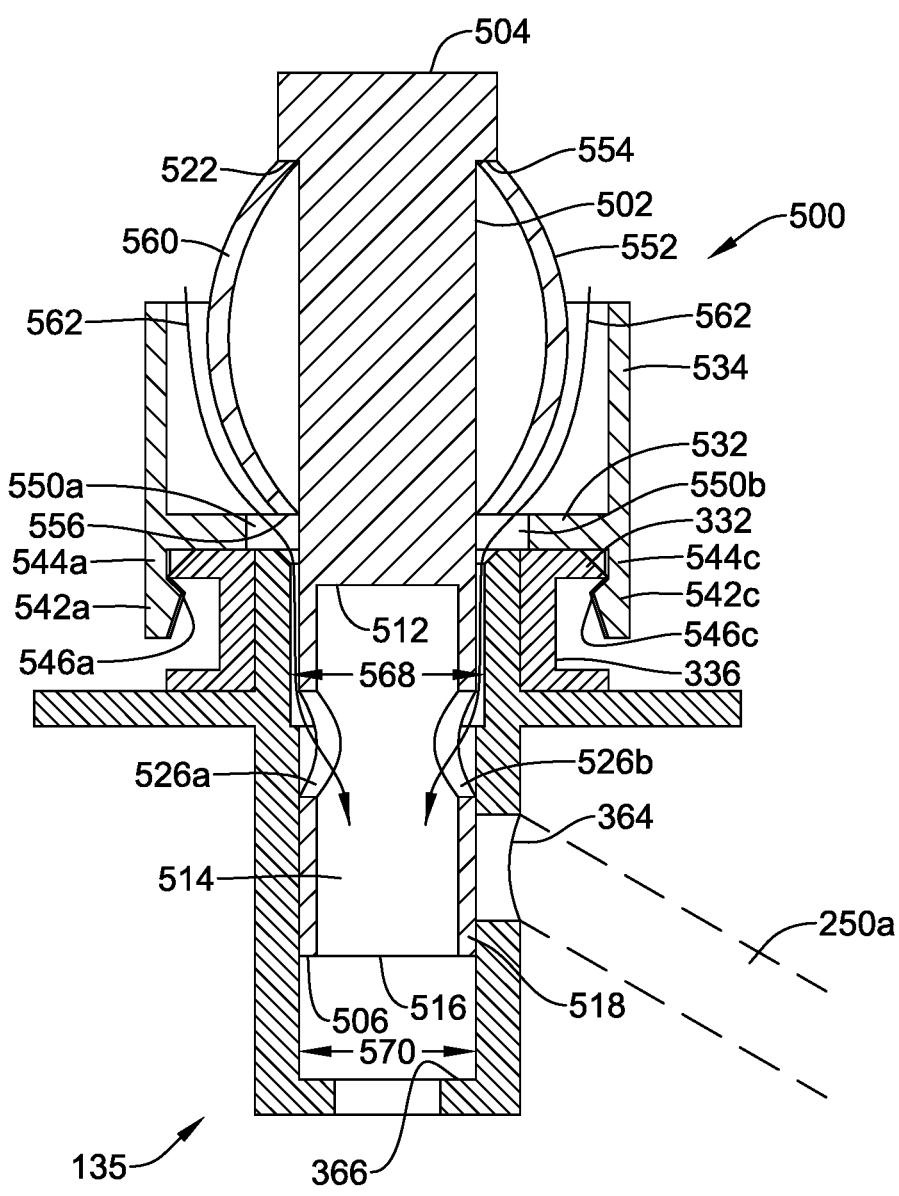
FIG. 17 depicts a schematic cross-sectional view of the illustrative suction valve of FIG. 14 assembled with a valve well and in a rest state or configuration.
Figure 18:
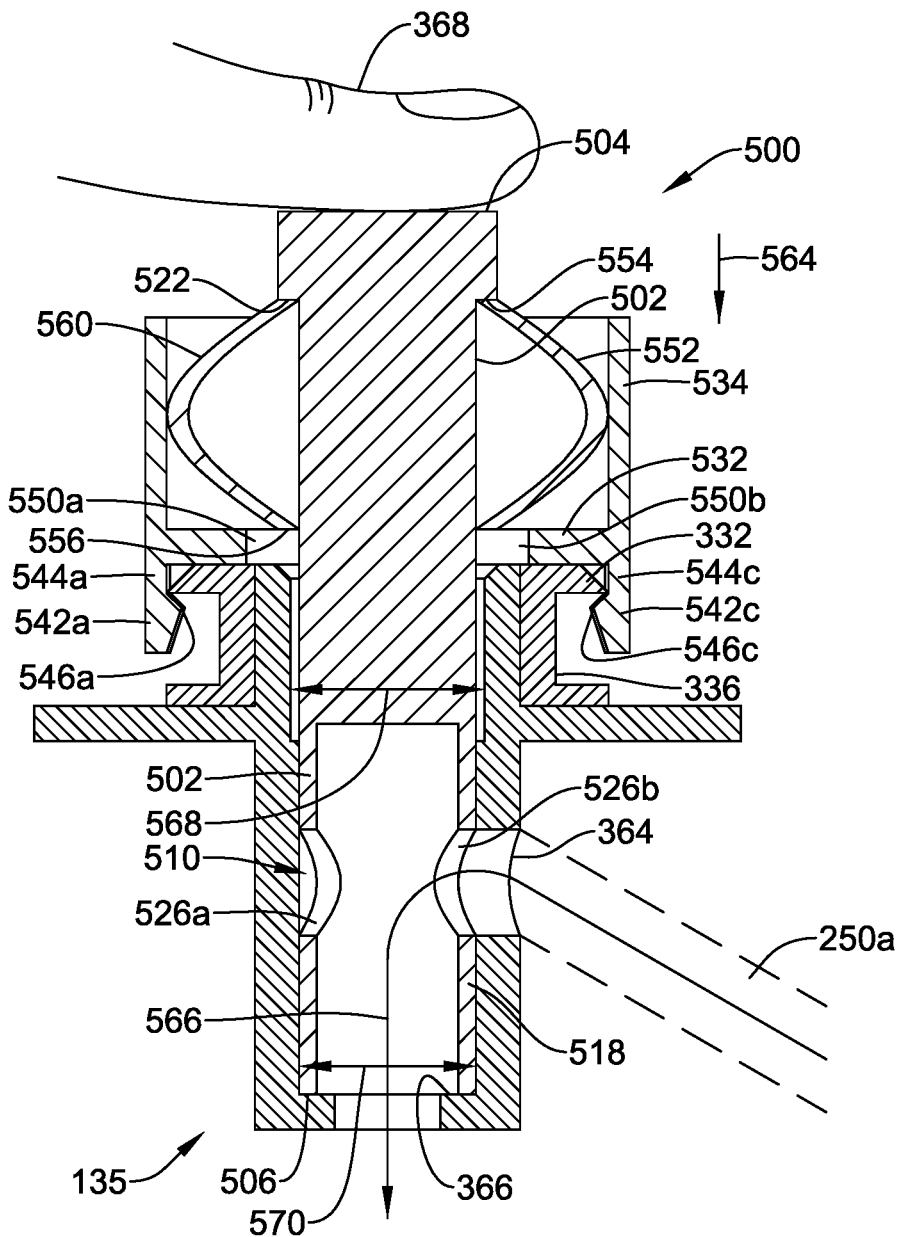
FIG. 18 depicts a schematic cross-sectional view of the illustrative suction valve of FIG. 14 assembled with a valve well and in an active state or use configuration.

Another illustrative suction valve 500 that may be used with the endoscope 100 and system 200 described herein will be described with respect to FIGS. 14-18. FIG. 14 depicts a top perspective view of an illustrative suction valve 500. FIG. 15 depicts a cross-sectional view of the illustrative suction valve 500, taken at line 15-15 of FIG. 14. FIG. 16 depicts a bottom perspective view of the illustrative suction valve 500. FIG. 17 depicts a schematic cross-sectional view of the illustrative suction valve 500 assembled with the valve well 135 and in a rest state or configuration. FIG. 18 depicts a schematic cross-sectional view of the illustrative suction valve 500 of FIG. 14 assembled with the valve well 135 and in an active state or use configuration.

The suction valve 500 may include an elongate shaft 502 extending from a first, or proximal, end 504 to a second, or distal, end 506. In some cases, the elongate shaft 502 may include a generally solid proximal end region 508 and a generally tubular distal end region 510. The elongate shaft 502 may transition from the generally solid proximal end region 508 to the generally tubular distal end region 510 at an intermediate transition region 512. A lumen 514 may extend from the transition region 512 to a distal opening 516 adjacent to the second end 506 of the elongate shaft 502. The distal end region 510 of the elongate shaft 502 may further include an annular sidewall 518. The lumen 514 and the annular sidewall 518 may extend less than an entire length of the elongate shaft 502 with the remaining portion of the elongate shaft 502 having a generally solid cross-section.

In some embodiments, an outer dimension or outer shape of the elongate shaft 502 may vary along the length thereof. For example, the elongate shaft 502 may have a generally circular cross-sectional shape adjacent to the first and second ends 504, 506 and a generally stadium shaped cross-sectional shape along an intermediate region 520. The stadium shape may have two generally parallel sides connected to one another at either end by a curved line. The intermediate region 520 may have a major dimension that is approximately equal to the diameter of the first and second ends 504, 506 and a minor dimension that is less than the diameter of the first and second ends 504, 506. The transition from the first circular cross-sectional shape adjacent the first end 504 to the stadium shaped cross-sectional shape may define one or more ledges 522. The transition from the second circular cross-sectional shape adjacent the distal end region 510 to the stadium shaped cross-sectional shape may also define one or more ledges 524. In other embodiments, the elongate shaft 502 may have a generally uniform cross-sectional shape along a length thereof.

The elongate shaft 502 may further include one or more apertures 526a, 526b extending through a thickness of the sidewall 518. The one or more apertures 526a, 526b may be positioned at an axial location between the transition region 512 and the second end 506 of the elongate shaft 502. The one or more apertures 526a, 526b may be configured to selectively fluidly couple the lumen 514 of the suction valve 500 with the suction supply line 250a, as will be described in more detail herein. In the illustrated embodiment, the elongate shaft 502 includes a first aperture 526a and a second aperture 526b. However, the elongate shaft 502 may include fewer than two or more than two apertures 526a, 526b, as desired. When two or more apertures 526a, 526b are provided, the apertures 526a, 526b may be positioned at similar axial locations along a longitudinal axis 528 of the elongate shaft 502 such that when the suction valve 500 is moved from the rest state or configuration (as shown in FIGS. 14-17) to an active state or use configuration (see, for example, FIG. 18), the apertures 526a, 526b will axially align with an opening 364 of the suction supply line 250a. The first and second apertures 526a, 526b may be circumferentially spaced about 180° from one another about the longitudinal axis 528 of the elongate shaft 502. However, other circumferential spacing intervals may be used as desired. It is contemplated that the circumferential spacing interval may be depend, at least in part, on a number of apertures 526a, 526b provided and/or orientation features configured to align the aperture(s) 526a, 526b with the suction supply line 250a.

The suction valve 500 may further include a rigid base member 530. The base member 530 may be formed from a material that does not readily undergo elastic deformation. Some illustrative materials may include, but are not limited to, polypropylene, polystyrene, nylon, polycarbonate, methacrylate, other polymers, metals, metal alloys, combinations thereof, etc. Generally, the base member 530 may have a generally planar platform region 532 and an annular wall 534. The annular wall 534 may extend from a first side 536 of the platform region 532 in a direction towards the first end 504 of the elongate shaft 502. The platform region 532 may have a generally circular outer shape with a central hole 540 (see, for example, FIG. 15) extending through a thickness of the platform region 532. The central hole 540 may be sized and shaped to slidably receive the elongate shaft 502 therethrough. While the platform region 532 is shown and described as having a generally circular outer shape, the platform region 532 may take other shapes as desired, such as, but not limited to, square, rectangular, polygonal, oblong, etc. It is contemplated that the shape of the platform region 532 may be determined, at least in part, by the shape of the valve well 135. For example, the shape of the platform region 532 may be similar to the shape of the valve well 135 to allow the base member 530 to rest on a flange 332 (see, for example, FIGS. 17 and 18) of the valve well 135. Similarly, the central hole 540 may have a generally stadium shaped cross-sectional shape similar to the stadium shape of the portion of the elongate shaft 502 disposed therein. However, the central hole 540 may take other cross-sectional shapes as desired, such as, but not limited to, circular, square, rectangular, polygonal, oblong, etc. It is contemplated that the shape of the central hole 540 may be determined, at least in part, by the outer shape of the region of the elongate shaft 502 disposed therein. The platform region 532 may extend radially outward from an outer surface of the elongate shaft 502. However, the platform region 532 and/or the base member 530 may be free from attachment to the outer surface of the elongate shaft 502 such that the elongate shaft 502 may be axially displaced along its longitudinal axis 528 while the base member 530 may be axially displaced to a lesser extent, or not at all.

The base member 530 may include one or more fastening members 542a-d configured to engage a flange 332 (see, for example, FIGS. 17 and 18) extending from a collar 336 of the valve well 135. In some embodiments, the fastening members 542a-d may be formed as a monolithic structure with the base member 530. In other embodiments, the fastening members 542a-d may be formed as separate structures from the base member 530 and subsequently attached thereto. The fastening members 542a-d may include an arm portion 544a-d extending from a second side 538 of the platform region 532 of the base member 530. The arm portions 544a-d may extend at an angle generally orthogonal to the platform region 532. However, this is not required. The arm portions 544a-d may extend at non-orthogonal angles, as desired. The arm portions 544a-d may each include a radially extending protrusion 546a-d. The sides of the arm portions 544a-d may include angles or slopes such that the protrusions 546a-d form a peak. The protrusions 546a-d may be configured engage a lower surface of the flange 332 while the sloped surfaces facilitate assembly and disassembly of the fastening members 542a-d with the flange 332. In some cases, the fastening members 542a-d may be clips configured to form a snap fit with the flange 332 of the valve well 135. For example, a second side 538 of the base member 530 may rest against an upper surface of the flange 332 while the fastening members 542a-d are configured to engage a lower surface of the flange 332.

The arm portions 544a-d of the fastening members 542a-d may flex or bend to allow the fastening members 542a-d to engage the flange 332. While the base member 530 is illustrated as including four fastening members 542a-d, the base member 530 may include fewer than four or more than four fastening members 542a-d, as desired. In the illustrated embodiment, the fastening members 542a-d are circumferentially spaced from one another by about 90°. However, this is not required. The fastening members 542a-d may be arranged in any uniform or non-uniform arrangement about a circumference of the base member 530. It is further contemplated that the fastening members 542a-d may be configured to engage the flange 332 in a threaded arrangement, a friction fit, a bayonet-style locking mechanism, etc.

The base member 530 may further include one or more orientation features 548a, 548b configured to align with mating orientation features 350a, 350b (see, for example, FIG. 6) in the collar 336 and/or flange 332 of the valve well

135. In some examples, the orientation features 548a, 548b may be axially extending legs or protrusions. In some embodiments, the orientation features 548a, 548b may be a curved protrusion configured to mate with a recess 350a, 350b formed in the curved wall of the collar 336, although this is not required. The orientation features 548a, 548b may extend at a generally orthogonal angle to the platform region 532 of the base member 530 or parallel to the longitudinal axis of the 528 of the elongate shaft 502. However, this is not required. The orientation features 548a, 548b may be sized, shaped, and oriented to align and mate with the corresponding features (e.g., recesses 350a, 350b) on the flange 332. While the base member 530 is illustrated as including a first and a second orientation feature 548a, 548b, the base member 530 may include fewer than two or more than two orientation features 548a, 548b, as desired. The orientation features 548a, 548b may be arranged in any uniform or non-uniform arrangement about a circumference of the base member 530. In the illustrated embodiment, the orientation features 548a, 548b are circumferentially spaced from one another by about 180°. However, this is not required. During assembly of the suction valve 500 with the valve well 135, the orientation features 548a, 548b may be aligned with mating recesses or slots 350a, 350b in the collar 336 of the valve well 135. The orientation features 548a, 548b and the mating slots 350a, 350b of the collar 336 may be positioned such that when the suction valve 500 is positioned within the valve well 135, at least one of the apertures 526a, 526b will align with the opening of the suction supply line 250a when the suction valve 500 is actuated to the active state or use configuration. In some examples, the orientation features 548a, 548b may be circumferentially aligned with the apertures 526a, 526b. In other examples, the orientation features 548a, 548b may be circumferentially offset from the apertures 526a, 526b, as illustrated in FIG. 16.

In some embodiments, the orientation features 548a, 548b may be combined with the fastening members 542a-d. For example, the suction valve 500 may be provided with one or more radially extending protrusions configured to mate with one or more "J" shaped slots in the collar 336 to form a bayonet style locking mechanism which both releasably secures the suction valve 500 to the valve well 135 as well as maintains proper orientation between the valve well 135 and the apertures 526a, 526b in the elongate shaft 502. The reverse configuration is also contemplated in which one or more "J" shaped slots are formed in the suction valve 500 and one or more protrusions extend from the collar 336 or flange 332. This is just one example. Other coupling mechanisms may be used, as desired.

The base member 530 may further include one or more openings or vent holes 550a, 550b extending through a platform region 532 thereof. The one or more openings 550a, 550b may be circumferentially spaced from one another. In the illustrated embodiment, the openings 550a, 550b are circumferentially spaced from one another by about 180°. However, this is not required. The openings 550a, 550b may be arranged in any uniform or non-uniform arrangement about the central hole 540 of the platform region 532 desired. In some examples, the openings 550a, 550b may contact or form a part of the central hole 540. In other examples, the openings 550a, 550b may be spaced anywhere between the central hole 540 and the annular wall 534. The openings 550a, 550b may allow the suction pump to draw air from atmosphere when the suction valve 500 is at rest.

The suction valve 500 may further include an actuation cap or compliant member 552 configured to flex or deform in response to a user input. The compliant member 552 may extend from a first end 554 adjacent to the first end 504 of the elongate shaft 502 to a second end 556 adjacent to a first or upper side 536 of the base member 530. The compliant member 552 may be fixedly coupled to the one or more upper ledges 522 of the elongate shaft 502 adjacent the first end 504 of the elongate shaft 502 or along a portion of the length of the elongate shaft 502 extending between the base member 530 and the first end 504 of the elongate shaft 502. The compliant member 552 may also be fixedly coupled to the first side 536 of the base member 530. In some embodiments, the second end 556 of the compliant member 552 may be coupled to the base member 530 at a radial location interior to the openings 550, although this is not required. The compliant member 552 may be positioned interior to the annular wall 534 of the base member 530. In some embodiments, the compliant member 552 may be overmolded with the elongate shaft 502 and the base member 530. However, other coupling techniques may be used, as desired.

The compliant member 552 may be formed from a material that allows the compliant member 552 to undergo elastic deformation in response to an applied force and return to a rest or original configuration in the absence of the applied force. The compliant member 552 may be formed from silicones, polyurethanes, or other soft durometer elastomers, rubbers or polymers. The cross-sectional dimension of the compliant member 552 may increase and then decrease from the first end 554 to the second end 556 thereof. In some examples, an outer surface of the compliant member 552 may take the shape of an ovoid or has a generally ellipsoidal outer surface. However, this is not required. In other examples, the compliant member 552 may have a generally hemispherical or dome-like shape in the rest configuration. The compliant member 552 may take yet other shapes, as desired, including, but not limited to, a truncated cone, cylindrical, rectangular prism, cubic, ovular, etc. It is further contemplated that the compliant member 552 may be generally solid, partially solid, or may define an open cavity 558 therein.

FIG. 17 depicts a schematic cross-section of the illustrative suction valve 500 of FIG. 14 positioned within a valve well 135 and in a rest state or configuration. For clarity, the valve well 135 is shown without the remaining portion of the endoscope handle 115. As described above, in the rest state, suction is not applied to the working channel 235 of the endoscope 100. Instead, the suction pump (not explicitly shown) draws air from the atmosphere via the openings or vent holes 550a, 550b of the base member 530 and into the lumen 514 of the elongate shaft 502 via the apertures 556a, 556b. To assemble the suction valve 500 with the valve well 135, the second end 506 of the elongate shaft 502 is inserted into the valve well 135. The suction valve 500 may be rotated as necessary to align the orientation features 548a, 548b of the suction valve 500 with the mating slots 350a, 350b in the collar 336 of the valve well 135. As the illustrated suction valve 500 includes two orientation features 548a, 548b circumferentially offset from one another by about 180° and each offset from the apertures 526a, 526b by about 90°, the suction valve 500 may be assembled with either the first aperture 526a or the second aperture 526b aligned with the suction supply line 250a. While not explicitly shown, the suction valve 500 may include visual indicia to facilitate assembly of the suction valve with the valve well 135. The elongate shaft 502 may be advanced into the valve well 135 until the second side 538 of the base member 530 contacts an upper surface of the flange 332. The downward movement of the suction valve 500 may allow the fastening members 542a-d to form a snap fit with or otherwise engage the flange 332 to prevent unintentional disengagement of the suction valve 500 from the valve well 135. However, the suction valve 500 may be removed from the valve well 135 with an applied force. For example, with sufficient upward force, the arm portions 544a-d may deflect radially outward to allow the suction valve 500 to be disassembled from the valve well 135.

In the rest configuration, as shown in FIG. 17, the apertures 526a, 526b are axially offset from the suction supply line 250a and the openings or vent holes 550a, 550b are open or unblocked. The suction pump (not explicitly shown) draws air from the atmosphere via the openings or vent holes 550a, 550b of the base member 530 and into the lumen 514 of the elongate shaft 502 via the apertures 556a, 556b, as shown at arrows 562. In some cases, air may also be drawn in via a gap between the second side 538 of the base member 530 and the surface of the flange 332. The sidewall 518 of the elongate shaft 502 blocks the opening 364 of the suction supply line 250a and precludes suction from being applied to the suction supply line 250a. In some embodiments, a proximal end of the valve well 135 may have a first cross-sectional dimension 568 and a distal end of the valve well 135 may have has a second cross-sectional dimension 570. The second cross-sectional dimension 570 of the valve well 135 may be less than the first cross-sectional dimension 568 of the valve well 135. This may allow the sidewall 518 to form a tight fit in the valve well 135 adjacent the opening 364 of the suction supply line 250a while allowing a gap between an outer surface of the elongate shaft 502 and the valve well 135 proximal to the apertures 526a, 526b to allow air to flow between the outer surface of the elongate shaft 502 and the valve well 135 and enter the lumen 514 via the apertures 526a, 526b.

FIG. 18 depicts a schematic cross-section of the illustrative suction valve 500 of FIG. 14 positioned within a valve well 135 and in an active state or use configuration. When suction within the working channel 235 is desired, the user may exert a downward or distal force, as shown at arrow 564 on the first end 504 of the elongate shaft 502 to move the elongate shaft 502 axially along or parallel to the longitudinal axis 528 of the elongate shaft 502 within the valve well 135. As the elongate shaft 502 is axially displaced, the sidewall 560 of the compliant member 552 may deform to allow the elongate shaft 502 to move. For example, the sidewall 560 may deform radially outward. When in the rest configuration, the compliant member 552 may have a first maximum cross-sectional dimension and when in the use configuration, the compliant member 552 may have a second maximum cross-sectional dimension. The second maximum cross-sectional dimension may be greater than the first maximum cross-sectional dimension such that the sidewall 560 may contact an inner surface of the annular wall 534 of the base member 530 to form a seal against the annular wall 334 and prevent air from being drawn in through the openings or vent holes 550a, 550b.

The elongate shaft 502 may be distally displaced within the valve well 135 to align at least one of the apertures 526a, 526b in the elongate shaft 502 with the opening 364 of the suction supply line 250a. In the illustrated embodiment, the second aperture 526b is aligned with the opening 364 of the suction supply line 250a to fluidly couple the suction pump with the suction supply line 250a and ultimately the working channel 235. However, as noted above, in some cases, the first aperture 526a may be aligned with the opening 364 of the suction supply line 250a. The base member 530 may be displaced downward into the flange 332 to the extent that there is a gap between the second side 538 of the base member 530 and the flange 332 prior to actuation of the elongate shaft 502. The base member 530 may not form a fluid-tight or gas-tight seal with the surface of the flange 332. However, air leaks at this base member 530/flange 332 interface may be negligible and not interfere with the ability of the suction pump to draw fluid or debris from the working channel 235. It is contemplated that the second side 538 of the base member 530 may include a gasket, O-ring, or other sealing member secured thereto to create a tighter seal between the second side 538 of the base member 530 and the surface of the flange 332.

It is contemplated that the apertures 526*a*, 526*b* may be located at an axial location along the elongate shaft 502 that allows at least one of the apertures 526*a*, 526*b* to be aligned with the opening 364 of the suction supply line 250*a* when the second end 506 of the elongate shaft 502 engages a flange 366 within the valve well 135. For example, the user may depress the first end 504 of the elongate shaft 502 until the second end 506 engages the radially inwardly extending flange 366. This may create a mechanical stop that indicates to the user the suction valve 500 is in the active state. In the active state or use configuration, as shown in FIG. 18, at least one of the apertures 526*a*, 526*b* (e.g., the second aperture 526*b* in the illustrated embodiment) is axially aligned with the opening 364 of the suction supply line 250*a* and the openings or vent holes 550*a*, 550*b* are is blocked or closed. For example, the interface between the sidewall 560 of the compliant member 552 and the annular wall 534 may prevent the suction pump from drawing air from atmosphere. It is further contemplated that the openings or vent holes 550*a*, 550*b* may be blocked by a portion of the compliant member 552 as the compliant member 552 is deformed. The suction pump (not explicitly shown) draws air from the suction supply line 250*a* (which is fluidly coupled to the working channel 235), as shown at arrow 566. This allows fluid or debris to be removed from the working channel 235 via the suction force from the suction pump. When the suction procedure is complete, the user may simply remove their finger 368 from the suction valve 500. The compliant member 552 may spring back or automatically return to the rest state with the apertures 526*a*, 526*b* and the opening 364 of the suction supply line 250*a* becomes misaligned, as shown in FIG. 17, without the use of a spring. It is contemplated that a change in diameter or shape of the elongate shaft 502 (e.g., the one or more lower ledges 524) may create a mechanical stop between the elongate shaft 502 and the rigid base 530 as the suction valve 500 is returning to the rest configuration.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising"

does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A suction valve for a medical device, the suction valve comprising:

an elongate shaft having a longitudinal axis and extending from a first end to a second end, the elongate shaft defining a lumen extending from the first end to the second end thereof;

at least one aperture extending through a sidewall of the elongate shaft;

a rigid base extending radially outward from an outer surface of the elongate shaft, the rigid base positioned between the first end and the second end of the elongate shaft;

at least one fastening member extending from the rigid base, the at least one fastening member configured to engage a mating feature on a medical device; and a compliant member extending between a first surface of the rigid base and the first end of the elongate shaft;

wherein in response to an applied force, the compliant member is configured to compress to move the elongate shaft in a downward direction parallel to the longitudinal axis of the elongate shaft to a use configuration and in the absence of the applied force the compliant member is configured to bias the elongate shaft in an upward direction to a rest configuration in which a top of the at least one aperture is downward from a bottom surface of the rigid base.

2. The suction valve of claim 1, further comprising one or more orientation features extending from a second surface of the rigid base.

3. The suction valve of claim 2, wherein the one or more orientation features comprise one or more protrusions extending parallel to the longitudinal axis to the elongate shaft.

4. The suction valve of claim 1, wherein the at least one fastening member is configured to form a snap fit with the mating feature on the medical device.

5. The suction valve of claim 1, wherein the at least one fastening member is formed as a single monolithic structure with the rigid base.

6. The suction valve of claim 1, wherein when the elongate shaft is in the use configuration, the at least one aperture is aligned with an opening of a medical device.

7. The suction valve of claim 1, wherein a top-most edge of the at least one aperture is below a bottom-most surface of the rigid base.

8. A suction valve for a medical device, the suction valve comprising:

an elongate shaft having a longitudinal axis and extending from a first end to a second end, the elongate shaft defining a lumen extending from the first end to the second end thereof;

at least one aperture extending through a sidewall of the elongate shaft;

a rigid base extending radially outward from an outer surface of the elongate shaft, the rigid base positioned between the first end and the second end of the elongate shaft;

a compliant member extending between a first surface of the rigid base and the first end of the elongate shaft; and at least one fastening member formed in the compliant member, the at least one fastening member configured to engage a mating feature on a medical device;

wherein in response to an applied force, the compliant member is configured to compress to move the elongate shaft in a downward direction parallel to the longitudinal axis of the elongate shaft to a use configuration and in the absence of the applied force the compliant member is configured to bias the elongate shaft in an upward direction to a rest configuration in which a top of the at least one aperture is downward from a bottom surface of the rigid base.

9. The suction valve of claim 8, wherein the compliant member has a cylindrical shape.

10. The suction valve of claim 8, wherein the at least one fastening member is formed as a single monolithic structure with the compliant member.

11. The suction valve of claim 8, wherein when the elongate shaft is in the use configuration, the at least one aperture is aligned with an opening of a medical device.

12. The suction valve of claim 8, further comprising one or more orientation features extending from a second surface of the rigid base.

13. A suction valve for a medical device, the suction valve comprising:

an elongate shaft having a longitudinal axis and extending from a first end to a second end, the elongate shaft defining a lumen extending second end towards the first end thereof;

at least one aperture extending through a sidewall of the elongate shaft;

a rigid base including a platform region extending radially outward from an outer surface of the elongate shaft and an annular wall extending from an outer edge of the platform region and towards the first end of the elongate shaft, the platform region including one or more openings extending through a thickness thereof; and a compliant member extending between a first surface of the platform region and one or more ledges adjacent the first end of the elongate tubular shaft;

wherein in response to an applied force, the compliant member is configured to compress to move the elongate shaft in a downward direction parallel to the longitudinal axis of the elongate shaft to a use configuration and in the absence of the applied force the compliant member is configured to bias the elongate shaft in an upward direction to a rest configuration in which a top of the at least one aperture is downward from a bottom surface of the rigid base.

14. The suction valve of claim 13, wherein when in the use configuration, the compliant member compresses to block the one or more openings in the platform region.

15. The suction valve of claim 13, wherein when in the use configuration, the complaint member deforms radially outward to contact an inner surface of the annular wall.

16. The suction valve of claim 13, wherein when in the rest configuration, the compliant member has a first cross-sectional dimension and when in the use configuration, the compliant member has a second cross-sectional dimension, the second cross-sectional dimension greater than the first cross-sectional dimension.

17. The suction valve of claim 13, further comprising one or more orientation features extending from a second surface of the rigid base.

18. The suction valve of claim 17, wherein the one or more orientation features comprise one or more protrusions extending parallel to the longitudinal axis to the elongate shaft.

19. The suction valve of claim 13, further comprising at least one fastening member extending from the rigid base, the at least one fastening member configured to engage a mating feature on a medical device.

20. The suction valve of claim 19, wherein the at least one fastening member is configured to form a snap fit with the mating feature on the medical device.

\* \* \* \* \*